US010314816B2

(12) United States Patent
Weibel et al.

(10) Patent No.: US 10,314,816 B2
(45) Date of Patent: Jun. 11, 2019

(54) ANTIMICROBIAL COMPOUNDS, COMPOSITIONS AND METHODS OF USE THEREOF

(71) Applicant: Wisconsin Alumni Research Foundation, Madison, WI (US)

(72) Inventors: Douglas Benjamin Weibel, Madison, WI (US); Ye Jin Eun, Cambridge, MA (US); Marie Hazel Foss, Hillsboro, OR (US); Katherine Ann Hurley, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 421 days.

(21) Appl. No.: 13/913,912

(22) Filed: Jun. 10, 2013

(65) Prior Publication Data
US 2013/0331424 A1 Dec. 12, 2013

Related U.S. Application Data

(60) Provisional application No. 61/657,126, filed on Jun. 8, 2012.

(51) Int. Cl.
*A61K 31/403* (2006.01)
*A61K 31/4045* (2006.01)
*C07D 209/04* (2006.01)
*C07D 209/44* (2006.01)
*C07D 209/60* (2006.01)

(52) U.S. Cl.
CPC ........ *A61K 31/403* (2013.01); *A61K 31/4045* (2013.01); *C07D 209/04* (2013.01); *C07D 209/44* (2013.01); *C07D 209/60* (2013.01)

(58) Field of Classification Search
CPC .............. A61K 31/403; A61K 31/4045; C07D 209/04; C07D 209/44; C07D 209/60
See application file for complete search history.

(56) References Cited

FOREIGN PATENT DOCUMENTS

| EP | 0711768 A1 | 5/1996 |
|----|------------|--------|
| FR | 2564465 | 11/1985 |
| JP | 2007223916 A * | 9/2007 |
| WO | 2009074733 A2 | 6/2009 |

OTHER PUBLICATIONS

Machine translation of JP 2007223916A (aquired Mar. 17, 2015), pp. 1-20.*
J. G. Cannon Chapter Nineteen in Burger's Medicinal Chemistry and Drug Discovery, Fifth Edition, vol. I: Principles and Practice, Wiley-Interscience 1995, pp. 783-802, 784.*
Sheridan, R.P. "The Most Common Chemical Replacements in Drug-Like Compounds", J. Chem. Inf. Comput. Sci., 2002, vol. 42, pp. 103-108.*
Coates et al.; "The Future Challenges Facing the Development of New Antimicrobial Drugs"; Nature Reviews; Drug Discovery; 1; pp. 895-910; (2002).
Coates et al.; "Targeting Non-Multiplying Organisms as a Way to Develop Novel Antimicrobials"; Trends Pharmacol Sci; 29(3); pp. 143-150; (2008).
Eun et al.; "DCAP: A Broad-Spectrum Antibiotic That Targets the Cytoplasmic Membrane of Bacteria"; Journal of the American Chemical Society; 134; pp. 11322-11325; (2012) plus supplemental information.
Ganzle M.G.; "Reutericyclin: Biological Activity, Mode of Action, and Potential Applications"; Appl Microbiol Biotechnol; 64; pp. 326-332; (2004).
Hurdle et al.; "Targeting Bacterial Membrane Function: an Underexploited Mechanism for Treating Persistent Infections"; Nature Reviews/ Microbiology; 9; pp. 62-72; (2011).
Novo et al.; "Multiparameter Flow Cytometric Analysis of Antibiotic Effects on Membrane Potential, Membrane Permeability, and Bacterial Counts of *Staphylococcus Aureus* and Micrococcus Luteus"; Antimicrobial Agents and Chemotherapy; 44; pp. 827-834; (2000).
Ooi et al.; "XF-70 and XF-73, Novel Antibacterial Agents Active Against Slow-Growing and Non-Dividing Cultures of *Staphylococcus Aureus* Including Biofilms"; J. Antimicrob Chemother; 65; pp. 72-78; (2010).
Orlov et al.; "Combination of the Electrogenic Ionophores, Valinomycin and CCCP, Can Lead to Non-Electrogenic K+/H+ Exchange on Bilayer Lipid Membranes"; FEBS Letters; 345; pp. 104-106; (1994).
Parsek et al.; "Bacterial Biofilms: An Emerging Link to Disease Pathogenesis"; Annu Rev. Microbiol.; 57; pp. 677-701; (2003).
Shapiro et al.; "Flow Cytometry of Bacterial Membrane Potential and Permeability"; Methods Mol Med.;142; pp. 175-186; (2008).
Strahl et al.; "Membrane Potential is Important for Bacterial Cell Division"; PNAS; 107(27); pp. 12281-12286; (2010).
Terada, Hiroshi; "Uncouplers of Oxidative Phosphorylation"; Environmental Health Perspectives; 87; pp. 213-218; (1990).
Thanbichler et al.; "MipZ, a Spatial Regulator Coordinating Chromosome Segregation with Cell Division in Caulobacter"; Cell; 126; pp. 147-162; (2006).
Eun et al.; "DCAP: A Broad-Spectrum Antibiotic That Targets the Cytoplasmic Membrane of Bacteria"; JACS; 134; pp. 11322-11325; (2012).
International Search Report and Written Opinion: International Application No. PCT/US2013/044929; International Filing Date Jun. 10, 2013; dated Aug. 16, 2013; 11 Pages.
Stefanska, et al.; "Antimicrobial Activity of 10-(diphenylmethylene)-4-azatricyclo[5.2.1.02,6]dec-8-ene-3,5-dione Derivatives"; Ann Microbiol; 60; pp. 151-155; (2010).

* cited by examiner

*Primary Examiner* — Kendra D Carter
(74) *Attorney, Agent, or Firm* — Cantor Colburn LLP

(57) ABSTRACT

Described herein are antimicrobial compounds identified via a high-throughput inhibitor screen of the in vitro activity of MipZ, which is an ATPase that regulates division site placement in *Caulobacter crescentus*. The compounds and their analogs are active against bacterial membranes and thus represent a novel class of antimicrobial compounds. The antimicrobial compounds are effective against both actively growing bacterial cells as well as bacterial cells in the stationary phase. The antimicrobial compounds are also effective against bacteria in biofilms.

13 Claims, 5 Drawing Sheets

Division plane assembly
FtsZ-GFP (green)

Step 1.
40,000 compounds screened using fluorescence polarization assay of MipZ ATPase activity Step 2.
Inhibitor identified

*Stereogenic center

ANTIMICROBIAL COMPOUNDS, COMPOSITIONS AND METHODS OF USE THEREOF

CROSS-REFERENCE TO RELATED APPLICATIONS

This application claims priority to U.S. Provisional Application Ser. No. 61/657,126 filed on Jun. 8, 2012.

STATEMENT REGARDING FEDERALLY SPONSORED RESEARCH & DEVELOPMENT

This invention was made with government support under 11-CRHF-0-6055 awarded by the USDA/NIFA and OD008735 awarded by the National Institutes of Health. The government has certain rights in the invention.

FIELD OF THE DISCLOSURE

The present disclosure is related to broad-spectrum antimicrobial compounds, pharmaceutical compositions comprising the antimicrobial compounds, and methods of treating bacterial infections with the antimicrobial compounds.

BACKGROUND

While the prevalence of multi-drug resistant pathogens continues to rise, the rate at which new clinical antimicrobials are introduced has declined significantly. In addition, the treatment of persistent infections has been complicated by pathogen phenotypes. Bacteria that grow very slowly are often associated with prolonged infections, and they are particularly tolerant to many of the clinically important classes of antibiotics that inhibit rapidly growing cells. For example, the β-lactam family of antibiotics inhibits enzymes involved in the synthesis of peptidoglycan, and is thus most effective at targeting microbes that grow rapidly and continuously synthesize new cell wall. Relying on antibiotics that require fast metabolism and growth creates long-term problems, as dormant bacteria, as well as those associated with biofilms and other multicellular structures, may survive antibiotic treatments, become predisposed to developing drug resistance, and cause a relapse.

An effective strategy for combating slow-growing bacteria is to target the lipid membrane. Proteomic analyses have demonstrated that approximately one third of all proteins in bacteria are associated with membranes. Peripheral and integral membrane proteins participate in various essential cellular processes, including: nutrient and waste transport, respiration, adhesion, mobility, cell-cell communication, and the transfer of genetic material. Compounds that perturb these processes disrupt growth and the maintenance of cell homeostasis and may serve as potent therapeutic antimicrobial agents.

Synthetic and naturally occurring small molecules that disrupt the bacterial membrane have been developed to treat persistent infections of Mycobacterial and Staphylococcal species. This class of compounds exhibits multiple mechanisms of action, including: the inhibition of specific enzymatic processes in the membrane, decreasing the transmembrane potential (ΔΨ), and increasing membrane permeability. The increase in permeability may act as a double-edged sword, as it perturbs bacterial physiology and facilitates the penetration of free radicals secreted by macrophages of the host immune system.

The therapeutic benefit of membrane-active drugs has been demonstrated against dormant bacteria; however, there are no clear design rules for small molecules that are specific for bacterial versus eukaryotic membranes. Many of the members of this class of antibiotics are ineffective against Gram-negative bacteria, presumably due to the outer membrane. The identification of new broad-spectrum antibiotics that target bacterial membranes and the study of their mechanism of toxicity would provide an important step forward for this field.

What are needed are new broad-spectrum antimicrobial compounds, particularly antimicrobial compounds that target bacterial membranes.

BRIEF SUMMARY

In one aspect, included herein is an antimicrobial compound of Formula I, or a pharmaceutically acceptable salt thereof:

$$G-Q-N(R^1)-C(R^2)(R^3)(R^4) \quad (I)$$

wherein

G is a heteroaryl, optionally substituted with 0, 1, 2, 3, or 4 substituents independently chosen from hydroxy, sulfate, nitro, amino, cyano, halogen, $C_1$-$C_4$ alkyl, $C_3$-$C_7$ cycloalkyl, $C_1$-$C_4$ alkoxy, mono- and di-($C_1$-$C_4$ alkyl)amino, $C_2$-$C_6$ alkoxycarbonyl, $C_2$-$C_6$ alkanoyl, carboxylic acid, $C_1$-$C_2$ haloalkyl, $C_1$-$C_2$ haloalkoxy, phenyl, pyridyl, heterocycloalkyl, alkylcarboxamide, $C_2$-$C_4$ alkenyl, or $C_2$-$C_4$ alkynyl;

Q is a $C_1$-$C_8$ hydrocarbon linking group comprising 0, 1, or 2 heteroatoms chosen from O, S, or $NR^4$, and wherein the linking group is substituted by 0, 1, 2, or 3 substituents independently chosen from hydroxy, sulfate, nitro, amino, cyano, halogen, $C_1$-$C_4$ alkyl, $C_3$-$C_7$ cycloalkyl, $C_1$-$C_4$ alkoxy, mono- and di-($C_1$-$C_4$ alkyl)amino, $C_2$-$C_6$ alkoxycarbonyl, $C_2$-$C_6$ alkanoyl, $C_1$-$C_2$ haloalkyl, $C_1$-$C_2$ haloalkoxy, or oxo;

$R^1$ is hydrogen, $C_1$-$C_8$ alkyl, $C_1$-$C_8$ haloalkyl, aryl, or (aryl)alkyl;

$R^2$ is hydrogen, $C_1$-$C_8$ alkoxy, $C_1$-$C_8$ haloalkyl, $C_1$-$C_8$ haloalkoxy, aryl, (aryl)alkyl, or $C_1$-$C_6$ alkyl optionally substituted with hydroxy, thiol (—SH), $C_1$-$C_8$ alkoxy;

$R^3$ is hydrogen, $C_1$-$C_8$ alkoxy, $C_1$-$C_8$ haloalkyl, $C_1$-$C_8$ haloalkoxy, aryl, (aryl)alkyl, or $C_1$-$C_6$ alkyl optionally substituted with hydroxy, thiol (—SH), $C_1$-$C_8$ alkoxy; and $R^4$ is hydrogen, $C_1$-$C_8$ alkoxy, $C_1$-$C_8$ haloalkyl, $C_1$-$C_8$ haloalkoxy, aryl, (aryl)alkyl, or $C_1$-$C_8$ alkyl optionally substituted with hydroxy, thiol (—SH), $C_1$-$C_8$ alkoxy; or $R^3$ and $R^4$ in —$C(R^2)(R^3)(R^4)$ together with the carbon (—C) form a cycloalkyl or heterocycloalkyl ring structure.

In another aspect, included herein are pharmaceutical compositions containing the compounds of formula I and methods of treating a subject in need of treatment for a bacterial infection comprising administering to the subject the pharmaceutical compositions.

In a further aspect, included herein are of methods inhibiting bacterial growth comprising contacting bacteria with an antimicrobially effective amount of a compound of Formula I.

Figure 1:
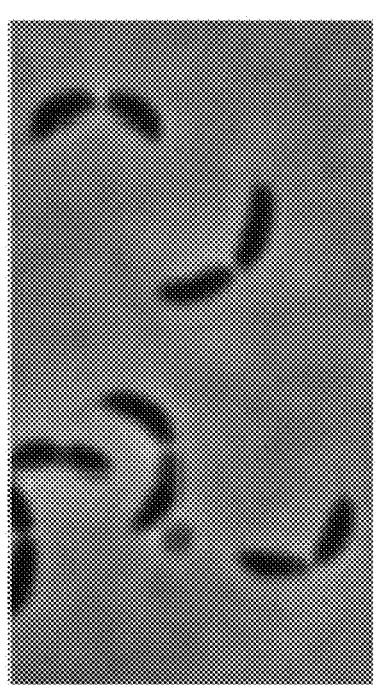
FIG. 1 is a schematic showing division plane assembly in *Caulobacter crescentus* and the concentration gradient of MipZ, which concentrates FtsZ at the division plane.

The above-described and other features will be appreciated and understood by those skilled in the art from the following detailed description, drawings, and appended claims.

DETAILED DESCRIPTION

Described herein is a family of compounds that specifically target the membranes of both Gram-positive and Gram-negative bacteria. In a specific embodiment, described herein is the compound, (2-((3-(3,6-dichloro-9H-carbazol-9-yl)-2-hydroxypropyl)amino)-2-(hydroxymethyl) propane-1,3-diol) (referred to as DCAP), and its derivatives. DCAP was identified via a high-throughput inhibitor screen of the in vitro activity of MipZ, which is an ATPase that regulates division site placement in *Caulobacter crescentus*. Using a strain of *C. crescentus* in which MipZ was translationally fused to yellow fluorescent protein (YFP), treatment of cells with DCAP (20 µM) caused MipZ-YFP to mislocalize. At high concentrations of DCAP (≥75 µM), cell lysis was observed within minutes after treatment. Without being held to theory, it is believed that DCAP does not specifically inhibit MipZ in the cell, but instead alters the properties of the cell envelope.

The chemical structure of DCAP is given below. The stereogenic center is marked with an *.

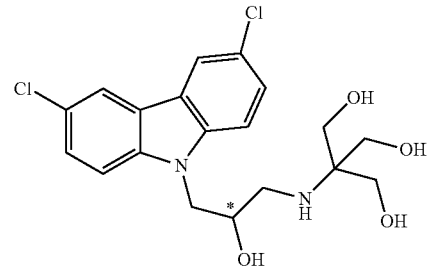 [SMILES: OCC(CO)(CO)NCC(O)Cn1c2ccc(Cl)cc2c2cc(Cl)ccc21]

In one embodiment, an antimicrobial compound has the Formula I, or a pharmaceutically acceptable salt thereof:

$$G-Q-N(R^1)-C(R^2)(R^3)(R^4) \quad (I)$$

wherein

G is a heteroaryl, optionally substituted with 0, 1, 2, 3, or 4 substituents independently chosen from hydroxy, sulfate, nitro, amino, cyano, halogen, $C_1$-$C_4$ alkyl, $C_3$-$C_7$ cycloalkyl, $C_1$-$C_4$ alkoxy, mono- and di-($C_1$-$C_4$ alkyl)amino, $C_2$-$C_6$ alkoxycarbonyl, $C_2$-$C_6$ alkanoyl, carboxylic acid, $C_1$-$C_2$ haloalkyl, $C_1$-$C_2$ haloalkoxy, phenyl, pyridyl, heterocycloalkyl, alkylcarboxamide, $C_2$-$C_4$ alkenyl, or $C_2$-$C_4$ alkynyl;

Q is a $C_1$-$C_8$ hydrocarbon linking group comprising 0, 1, or 2 heteroatoms chosen from O, S, or $NR^4$, and wherein the linking group is substituted by 0, 1, 2, or 3 substituents independently chosen from hydroxy, sulfate, nitro, amino, cyano, halogen, $C_1$-$C_4$ alkyl, $C_3$-$C_7$ cycloalkyl, $C_1$-$C_4$ alkoxy, mono- and di-($C_1$-$C_4$ alkyl)amino, $C_2$-$C_6$ alkoxycarbonyl, $C_2$-$C_6$ alkanoyl, $C_1$-$C_2$ haloalkyl, $C_1$-$C_2$ haloalkoxy, or oxo;

$R^1$ is hydrogen, $C_1$-$C_8$ alkyl, $C_1$-$C_8$ haloalkyl, aryl, or (aryl)alkyl;

$R^2$ is hydrogen, $C_1$-$C_8$ alkoxy, $C_1$-$C_8$ haloalkyl, $C_1$-$C_8$ haloalkoxy, aryl, (aryl)alkyl, or $C_1$-$C_8$ alkyl optionally substituted with hydroxy, thiol (—SH), $C_1$-$C_8$ alkoxy;

$R^3$ is hydrogen, $C_1$-$C_8$ alkoxy, $C_1$-$C_8$ haloalkyl, $C_1$-$C_8$ haloalkoxy, aryl, (aryl)alkyl, or $C_1$-$C_8$ alkyl optionally substituted with hydroxy, thiol (—SH), $C_1$-$C_8$ alkoxy; and $R^4$ is hydrogen, $C_1$-$C_8$ alkoxy, $C_1$-$C_8$ haloalkyl, $C_1$-$C_8$ haloalkoxy, aryl, (aryl)alkyl, or $C_1$-$C_8$ alkyl optionally substituted with hydroxy, thiol (—SH), $C_1$-$C_8$ alkoxy; or $R^3$ and $R^4$ in —$C(R^2)(R^3)(R^4)$ together with the carbon (—C) form a $C_3$-$C_7$ cycloalkyl or heterocycloalkyl ring structure.

Within this embodiment, G is carbazole, 9,10-dihydroacridine, acridin-9(10H)-one, indole, isoindole, indoline, benzimidazole, indazole, purine, 1,2,3,4-tetrahydroquinoline or 1,2,3,4-tetrahydroisoquinoline, each optionally substituted with 0, 1, 2, 3, or 4 substituents independently chosen from hydroxy, sulfate, nitro, amino, cyano, halogen, $C_1$-$C_4$ alkyl, $C_3$-$C_7$ cycloalkyl, $C_1$-$C_4$ alkoxy, mono- and di-($C_1$-$C_4$ alkyl)amino, $C_2$-$C_6$ alkoxycarbonyl, $C_2$-$C_6$ alkanoyl, carboxylic acid, $C_1$-$C_2$ haloalkyl, $C_1$-$C_2$ haloalkoxy, phenyl, pyridyl, heterocycloalkyl, alkylcarboxamide, $C_2$-$C_4$ alkenyl, or $C_2$-$C_4$ alkynyl.

Within this embodiment, $R^1$ is hydrogen, $C_1$-$C_6$ alkyl, $C_1$-$C_6$ haloalkyl, aryl, or (aryl)alkyl;

$R^2$ is hydrogen, $C_1$-$C_6$ alkoxy, $C_1$-$C_6$ haloalkyl, $C_1$-$C_6$ haloalkoxy, aryl, (aryl)alkyl, or $C_1$-$C_6$ alkyl optionally substituted with hydroxy, thiol (—SH), $C_1$-$C_6$ alkoxy;

$R^3$ is hydrogen, $C_1$-$C_6$ alkoxy, $C_1$-$C_6$ haloalkyl, $C_1$-$C_6$ haloalkoxy, aryl, (aryl)alkyl, or $C_1$-$C_6$ alkyl optionally substituted with hydroxy, thiol (—SH), $C_1$-$C_6$ alkoxy; and $R^4$ is hydrogen, $C_1$-$C_6$ alkoxy, $C_1$-$C_6$ haloalkyl, $C_1$-$C_6$ haloalkoxy, aryl, (aryl)alkyl, or $C_1$-$C_6$ alkyl optionally substituted with hydroxy, thiol (—SH), $C_1$-$C_6$ alkoxy; or $R^3$ and $R^4$ in —C($R^2$)($R^3$)($R^4$) together with the carbon (—C) form a $C_3$-$C_7$ cycloalkyl.

Further within this embodiment, $R^1$ is hydrogen, methyl, or ethyl.

Still further within this embodiment, $R^2$, $R^3$, and $R^4$ are each independently hydrogen, methyl, ethyl, n-propyl, isopropyl, n-butyl, sec-butyl, pentyl, isopentyl, —CH$_2$OH, —CH$_2$SH, —CH$_2$CH$_2$OH, —CH$_2$CH$_2$SH, —OCH$_3$, —OCH$_2$CH$_3$, —CH$_2$OCH$_3$, —CH$_2$SCH$_3$, or $R^2$ is hydrogen and $R^3$ and $R^4$ in —C($R^2$)($R^3$)($R^4$) together with the carbon (—C) form a cyclohexyl.

In another embodiment, the inhibitor includes compounds and pharmaceutically acceptable salts of Formula Ia to Ih:

(Ia)

(Ib)

(Ic)

(Id)

(Ie)
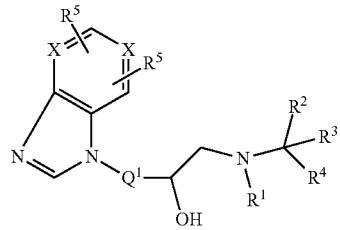

(If)
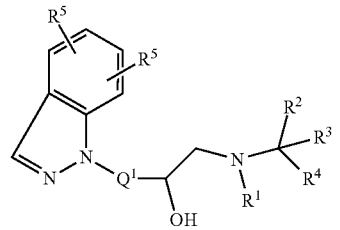

(Ig)
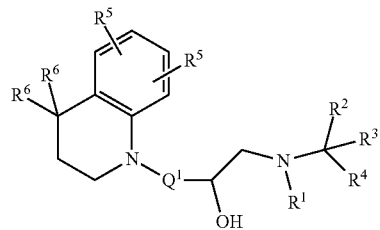

(Ih)
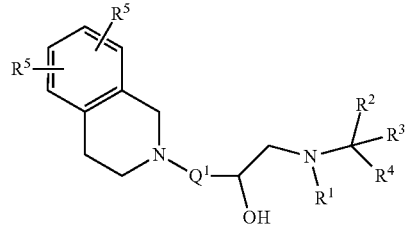

wherein $R^1$, $R^2$, $R^3$, and $R^4$, are as previously defined, $Q^1$ is a $C_1$-$C_6$ hydrocarbon linking group comprising 0, 1, or 2 heteroatoms chosen from O, S, or NR$^4$, and wherein the linking group is substituted by 0, 1, 2, or 3 substituents independently chosen from hydroxy, sulfate, nitro, amino, cyano, halogen, $C_1$-$C_4$ alkyl, $C_3$-$C_7$ cycloalkyl, $C_1$-$C_4$ alkoxy, mono- and di-($C_1$-$C_4$ alkyl)amino, $C_2$-$C_6$ alkoxycarbonyl, $C_2$-$C_6$ alkanoyl, $C_1$-$C_2$ haloalkyl, $C_1$-$C_2$ haloalkoxy, or oxo;

each instance of $R^5$ independently is hydrogen, hydroxy, sulfate, nitro, amino, cyano, halogen, $C_1$-$C_4$ alkyl, $C_3$-$C_7$ cycloalkyl, $C_1$-$C_4$ alkoxy, mono- and di-($C_1$-$C_4$ alkyl)amino, $C_2$-$C_6$ alkoxycarbonyl, $C_2$-$C_6$ alkanoyl, carboxylic acid, $C_1$-$C_2$ haloalkyl, $C_1$-$C_2$ haloalkoxy, phenyl, pyridyl, heterocycloalkyl, alkylcarboxamide, $C_2$-$C_4$ alkenyl, or $C_2$-$C_4$ alkynyl;

each instance of $R^6$ independently is hydrogen, hydroxy, sulfate, nitro, amino, cyano, halogen, $C_1$-$C_4$ alkyl, $C_3$-$C_7$ cycloalkyl, $C_1$-$C_4$ alkoxy, mono- and di-($C_1$-$C_4$ alkyl)amino, $C_2$-$C_6$ alkoxycarbonyl, $C_2$-$C_6$ alkanoyl, carboxylic acid, $C_1$-$C_2$ haloalkyl, $C_1$-$C_2$ haloalkoxy, phenyl, pyridyl, heterocycloalkyl, alkylcarboxamide, $C_2$-$C_4$ alkenyl, or $C_2$-$C_4$ alkynyl, or wherein both $R^6$ form oxo (i.e., =O);

each instance of X is N, CH, or CR$^5$; and

⋯ is a single or double bond.

Exemplary G, Q, and —N(R')—C(R²)(R³)(R⁴) groups are provided in the following tables.
$$G\text{-}Q\text{-}N(R^1)\text{—}C(R^2)(R^3)(R^4) \qquad (I)$$
| G |
|---|
| 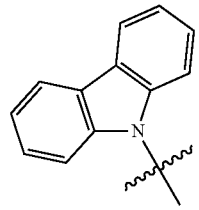 [SMILES: *n1c2ccccc2c2ccccc21] |
| 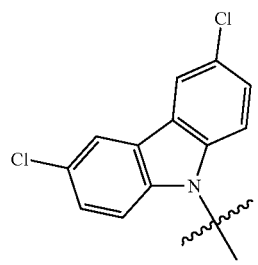 [SMILES: *n1c2ccc(Cl)cc2c2cc(Cl)ccc21] |
| 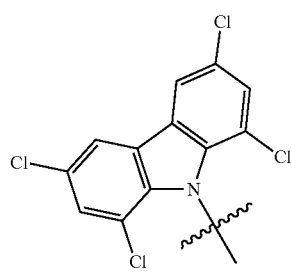 [SMILES: *n1c2c(Cl)cc(Cl)cc2c2cc(Cl)cc(Cl)c21] |
| 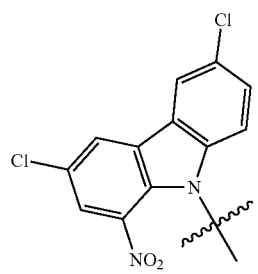 [SMILES: *n1c2ccc(Cl)cc2c2cc(Cl)cc([N+](=O)[O-])c21] |
| 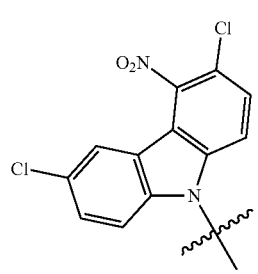 [SMILES: *n1c2ccc(Cl)cc2c2c([N+](=O)[O-])c(Cl)ccc21] |
-continued
| G |
|---|
| 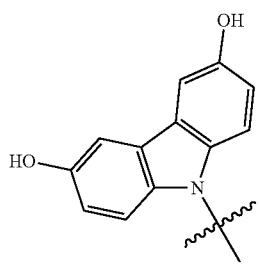 [SMILES: *n1c2ccc(O)cc2c2cc(O)ccc21] |
| 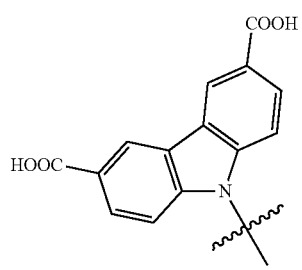 [SMILES: *n1c2ccc(C(=O)O)cc2c2cc(C(=O)O)ccc21] |
| 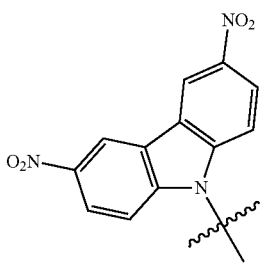 [SMILES: *n1c2ccc([N+](=O)[O-])cc2c2cc([N+](=O)[O-])ccc21] |
| 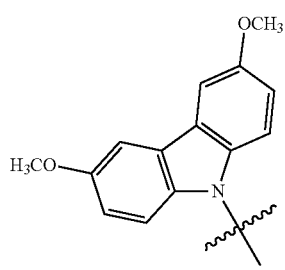 [SMILES: *n1c2ccc(OC)cc2c2cc(OC)ccc21] |
| 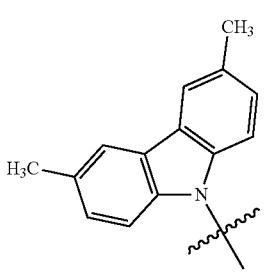 |

-continued
G
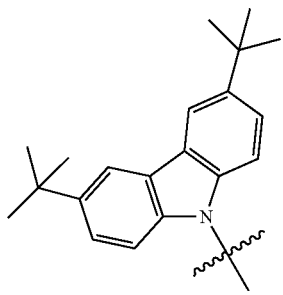 [SMILES: *n1c2ccc(C(C)(C)C)cc2c2cc(C(C)(C)C)ccc21]
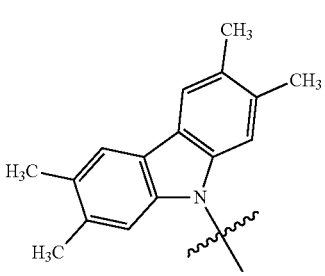
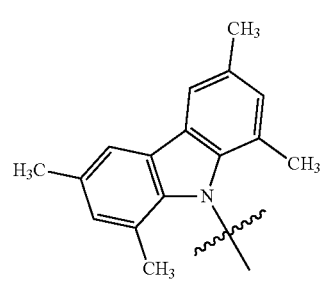
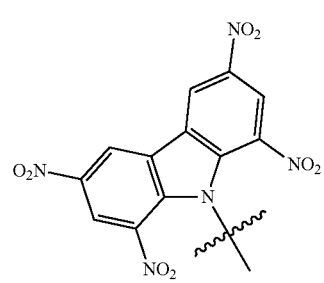 [SMILES: *n1c2c([N+](=O)[O-])cc([N+](=O)[O-])cc2c2cc([N+](=O)[O-])cc([N+](=O)[O-])c21]
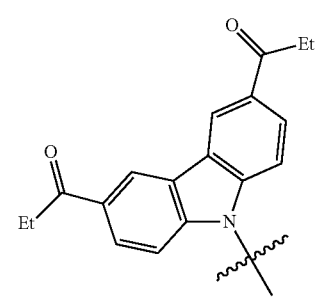 [SMILES: *n1c2ccc(C(=O)CC)cc2c2cc(C(=O)CC)ccc21]
-continued
G
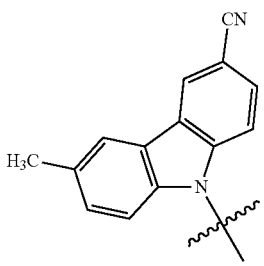 [SMILES: *n1c2ccc(C)cc2c2cc(C#N)ccc21]
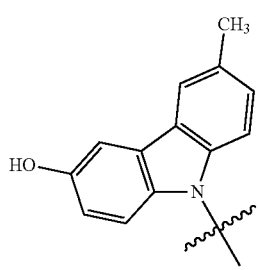 [SMILES: *n1c2ccc(C)cc2c2cc(O)ccc21]
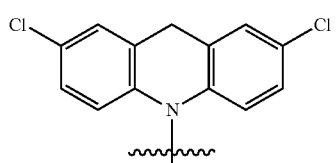
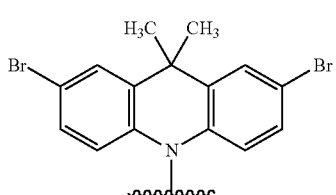
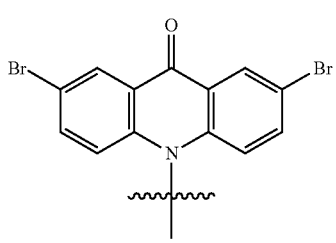 [SMILES: *n1c2ccc(Br)cc2c(=O)c2cc(Br)ccc21]
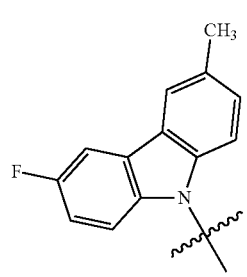 [SMILES: *n1c2ccc(C)cc2c2cc(F)ccc21]

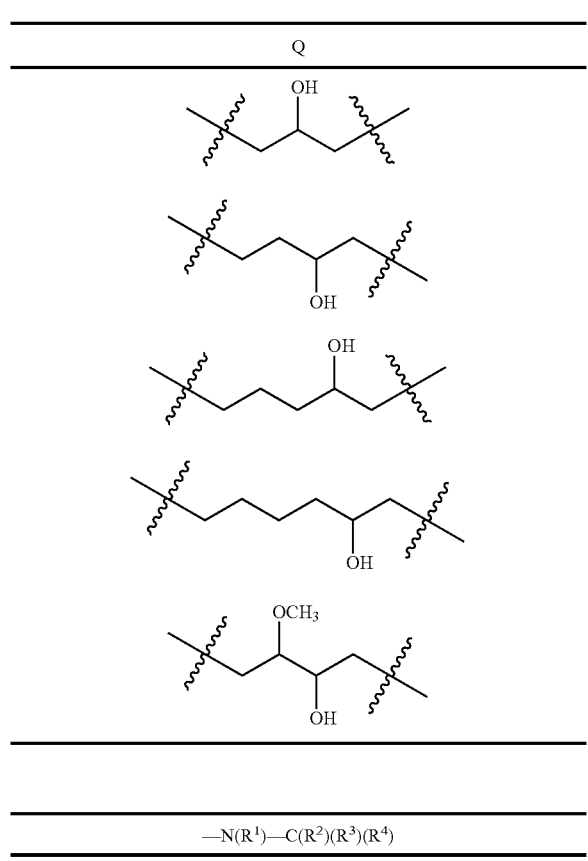
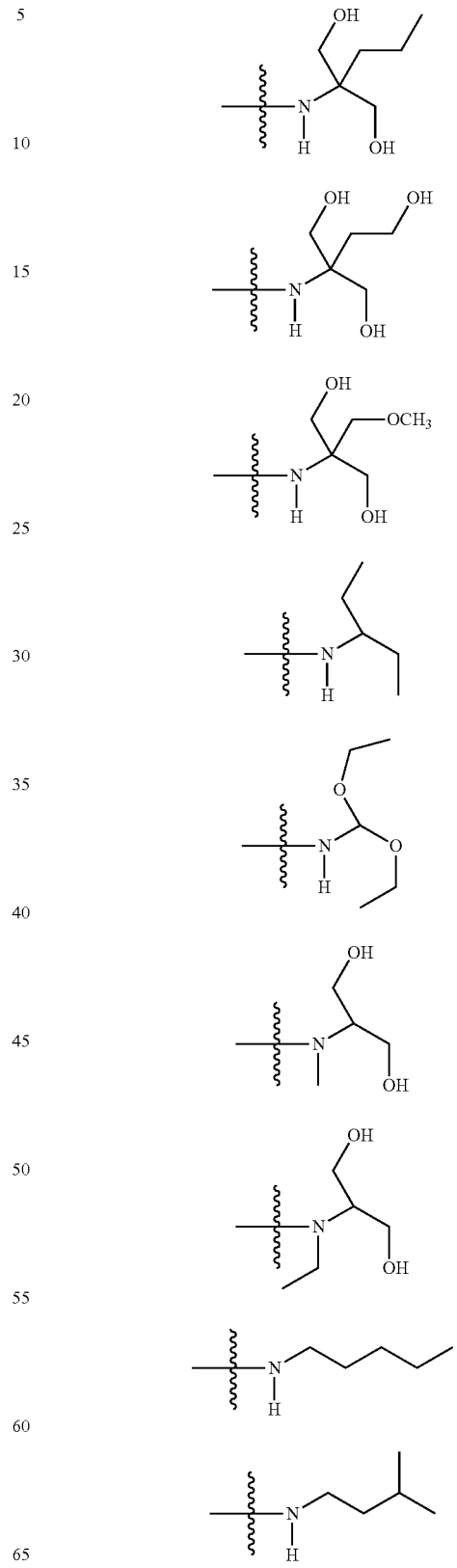

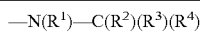

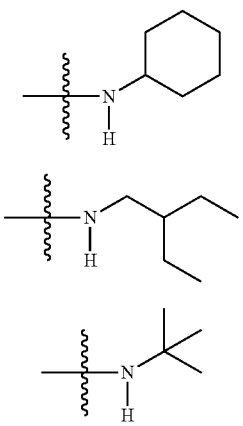

In certain situations, the compounds of Formulae I, Ia, and Ib may possess asymmetry so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. In these situations, the single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral LC or HPLC column.

The term "substituted", as used herein, means that any one or more hydrogens on the designated atom or group is replaced with a selection from the indicated group, provided that the designated atom's normal valence is not exceeded. When a substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

A dash ("—") that is not between two letters or symbols is used to indicate a point of attachment for a substituent. For example, —COOH is attached through the carbon atom.

As used herein, "alkyl" is intended to include both branched and straight-chain saturated aliphatic hydrocarbon groups, having the specified number of carbon atoms. Thus, the term $C_1$-$C_8$ alkyl as used herein includes alkyl groups having from 1 to about 8 carbon atoms. When $C_0$-$C_n$ alkyl is used herein in conjunction with another group, for example, phenyl$C_0$-$C_4$alkyl, the indicated group, in this case phenyl, is either directly bound by a single covalent bond ($C_0$), or attached by an alkyl chain having the specified number of carbon atoms, in this case from 1 to about 2 carbon atoms. Examples of alkyl include, but are not limited to, methyl, ethyl, n-propyl, isopropyl, n-butyl, t-butyl, n-pentyl, and sec-pentyl.

"Alkenyl" as used herein, indicates hydrocarbon chains of either a straight or branched configuration comprising one or more unsaturated carbon-carbon bonds, which may occur in any stable point along the chain, such as ethenyl and propenyl.

"Alkynyl" as used herein, indicates hydrocarbon chains of either a straight or branched configuration comprising one or more triple carbon-carbon bonds that may occur in any stable point along the chain, such as ethynyl and propynyl.

"Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Alkanoyl" indicates an alkyl group as defined above, attached through a keto (—(C=O)—) bridge. Alkanoyl groups have the indicated number of carbon atoms, with the carbon of the keto group being included in the numbered carbon atoms. For example a $C_2$alkanoyl group is an acetyl group having the formula $CH_3(C=O)$—.

The term "alkoxycarbonyl" indicates an alkoxy group, as defined above, having the indicated number of carbon atoms, attached through a keto linkage. The carbon of the keto linker is not included in the numbering, thus a $C_2$alkoxycarbonyl has the formula $CH_3CH_2O(C=O)$—.

The term "alkylcarboxamide" indicates an alkyl group, as defined above, having the indicated number of carbon atoms, attached through a carboxamide linkage, i.e., a —$CONH_2$ linkage, where one or both of the amino hydrogen is replace by an alkyl group. Alkylcarboxamide groups may be mono- or di-alkylcarboxamide groups, such an ethylcarboxamide or dimethylcarboxamide.

As used herein, the term "mono- or di-alkylamino" indicates secondary or tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propyl-amino.

As used herein, the term "aryl" indicates aromatic groups containing only carbon in the aromatic ring or rings. Such aromatic groups may be further substituted with carbon or non-carbon atoms or groups. Typical aryl groups contain 1 to 3 separate, fused, or pendant rings and from 6 to about 18 ring atoms, without heteroatoms as ring members. Where indicated aryl groups may be substituted. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and bi-phenyl.

In the term "(aryl)alkyl", aryl and alkyl are as defined above, and the point of attachment is on the alkyl group. This term encompasses, but is not limited to, benzyl, phenylethyl, and piperonyl. Likewise, in the term (aryl)carbhydryl, aryl and carbhydryl are as defined above and the point of attachment is on the carbhydryl group, for example a phenylpropen-1-yl group.

"Carbhydryl" as used herein, includes both branched and straight-chain hydrocarbon groups, which are saturated or unsaturated, having the specified number of carbon atoms.

"Cycloalkyl" as used herein, indicates saturated hydrocarbon ring groups, having the specified number of carbon atoms, usually from 3 to about 8 ring carbon atoms, or from 3 to about 7 carbon atoms. Examples of cycloalkyl groups include cyclopropyl, cyclobutyl, cyclopentyl, or cyclohexyl as well as bridged or caged saturated ring groups such as norbornane or adamantane.

"Haloalkyl" indicates both branched and straight-chain saturated aliphatic hydrocarbon groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined above attached through an oxygen bridge.

"Halo" or "halogen" as used herein refers to fluoro, chloro, bromo, or iodo.

As used herein, "heteroaryl" indicates a stable 5- to 7-membered monocyclic, 7- to 10-membered bicyclic, or 10- to 15-membered heterocyclic ring which contains at least 1 aromatic ring that contains from 1 to 4, or preferably from 1 to 3, heteroatoms chosen from N, O, and S, with remaining ring atoms being carbon. When the total number of S and O atoms in the heteroaryl group exceeds 1, these heteroatoms are not adjacent to one another. It is preferred that the total number of S and O atoms in the heteroaryl group is not more than 2. Examples of heteroaryl groups include, but are not limited to, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, and 5,6,7,8-tetrahydroisoquinoline. In the term "heteroarylalkyl," heteroaryl and alkyl are as defined above, and the point of attachment is on the alkyl group. This term encompasses, but is not limited to, pyridylmethyl, thiophenylmethyl, and pyrrolyl(1-ethyl).

The term "heterocycloalkyl" is used to indicate saturated cyclic groups containing from 1 to about 5 heteroatoms chosen from N, O, and S, with remaining ring atoms being carbon. Heterocycloalkyl groups have from 3 to about 8 ring atoms, and more typically have from 5 to 7 ring atoms. A $C_2$-$C_7$ heterocycloalkyl group contains from 2 to about 7 carbon ring atoms and at least one ring atom chosen from N, O, and S. Examples of heterocycloalkyl groups include morpholinyl, piperazinyl, piperidinyl, and pyrrolidinyl groups.

"Pharmaceutically acceptable salts" includes derivatives of the disclosed compounds wherein the parent compound is modified by making an acid or base salt thereof, and further refers to pharmaceutically acceptable solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional salts and the quaternary ammonium salts of the parent compound formed, for example, from inorganic or organic acids. For example, conventional acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. The pharmaceutically acceptable salts of the present invention can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable.

In one aspect, provided herein are methods of treating a subject in need of treatment for a bacterial infection, comprising administering to the individual an antimicrobial compound or composition as described herein. The bacteria can be actively growing or in the stationary phase.

The bacteria causing the infection can be Gram-negative, Gram-positive, or bacteria that are neither Gram-negative nor Gram-positive. Gram-negative bacteria include *Escherichia coli, Caulobacter crescentus, Pseudomonas aeruginosa, Agrobacterium tumefaciens, Branhamella catarrhalis, Citrobacter diversus, Enterobacter aerogenes, Klebsiella pneumoniae, Proteus mirabilis, Salmonella typhimurium, Neisseria meningitidis, Serratia marcescens, Shigella sonnei, Shigella boydii, Neisseria gonorrhoeae, Acinetobacter baumannii, Salmonella enteriditis, Fusobacterium nucleatum, Veillonella parvula, Bacteroides forsythus, Actinobacillus actinomycetemcomitans, Aggregatibacter actinomycetemcomitans, Porphyromonas gingivalis, Helicobacter pylori, Francisella tularensis, Yersinia pestis, Vibrio cholera, Morganella morganii, Edwardsiella tarda, Acinetobacter baumannii* and *Haemophilus influenzae*. In another embodiment, the bacteria are Gram-positive bacteria. Gram-positive bacteria include species of *Bacillus, Listeria, Staphylococcus, Streptococcus, Enterococcus, Corynebacterium, Propionibacterium* and *Clostridium*. Specific Gram-positive bacteria include *Staphylococcus aureus, Staphylococcus epidermidis, Enterococcus faecium*, and *Bacillus cereus*. In a specific embodiment, the bacteria are one or more drug resistant bacteria. Bacteria that are neither Gram-negative nor Gram-positive include *Mycobacterium leprae, Mycobacterium tuberculosis* and other *Mycobacteria*. Further included are bacteria such as *Chlamydia* and *Mycoplasma* that do not have a cell wall.

In another aspect, a method of inhibiting bacterial growth comprises contacting the bacteria with an antimicrobial compound as described herein. The bacteria can be actively growing or in the stationary phase. Methods of inhibiting bacteria include methods useful for treatment of a subject (human or veterinary) and also include methods useful for inhibiting bacteria outside of a subject, such as use for sterilization and disinfection.

In one embodiment, the bacteria are in the form of a biofilm. A biofilm is a complex aggregate of microorganisms such as bacteria, wherein the cells adhere to each other on a surface. The cells in biofilms are physiologically distinct from planktonic cells of the same organism, which are single cells that can float or swim in liquid medium. Biofilms are involved in, for example, urinary tract infections, middle ear infections, dental plaques, gingivitis, coatings of contact lenses, cystic fibrosis, and infections of joint prostheses and heart valves.

The antimicrobial compounds and compositions may be administered prophylactically, chronically, or acutely. For example, such compounds may be administered prophylactically to patients known to be prone to bacterial infections, or who are known to have been exposed to potentially infectious agents. The compounds may also be administered prophylactically to patients suffering other conditions, such as AIDS or other immune-system-suppressing conditions that render them susceptible to opportunistic infections. In addition to the prevention of such infections, chronic administration of the antimicrobial compounds will typically be indicated in treating refractory conditions, such as persistent infection by multiple drug-resistant strains of bacteria. Acute administration of the antimicrobial compounds is indicated to treat, for example, those subjects presenting with classical indications of bacterial infection.

As used herein, "contacting" means that a compound is provided such that it is capable of making physical contact with another element, such as a microorganism, a microbial culture or a substrate. In another embodiment, the term "contacting" means that the compound is introduced into a subject receiving treatment, and the compound is allowed to come in contact in vivo. Thus, contacting can include administration of a compound, that is, introducing the compound into the body, such as into the systemic circulation. Administration routes include but are not limited to, rectal, oral, buccal, sublingual, pulmonary, transdermal, transmucosal, as well as subcutaneous, intraperitoneal, intravenous, and intramuscular injection.

Since the antimicrobial compounds are antibacterially active and inhibit bacterial growth, they are also of use in treating bacterial contamination of a substrate, such as hospital instruments or work surfaces. In order to treat a contaminated substrate, the compounds may be applied to the site of such contamination in an amount sufficient to inhibit bacterial growth.

In certain embodiments, the compounds are administered to a patient or subject. A "patient" or "subject", used equivalently herein, means mammals and non-mammals. "Mammals" means a member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

The phrase "effective amount," as used herein, means an amount of an agent, which is sufficient enough to significantly and positively modify symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

The phrase "inhibitory amount", as used herein, means an amount of an agent (a compound or composition), which is sufficient to reduce the level or activity of bacterial infection to a statistically significant lesser value as compared to when the agent is not present.

The amount of compound effective for any indicated condition will, of course, vary with the individual subject being treated and is ultimately at the discretion of the medical or veterinary practitioner. The factors to be considered include the condition being treated, the route of administration, the nature of the formulation, the subject's body weight, surface area, age and general condition, and the particular compound to be administered. In general, a suitable effective dose is in the range of about 0.1 to about 500 mg/kg body weight per day, preferably in the range of about 5 to about 350 mg/kg per day. The total daily dose may be given as a single dose, multiple doses, e.g., two to six times per day, or by intravenous infusion for a selected duration. Dosages above or below the range cited above may be administered to the individual patient if desired and necessary.

Also included herein are pharmaceutical compositions comprising the antimicrobial compounds. As used herein, "pharmaceutical composition" means a therapeutically effective amount of the compound together with a pharmaceutically acceptable excipient, such as a diluent, preservative, solubilizer, emulsifier, adjuvant, and the like. As used herein "pharmaceutically acceptable excipients" are well known to those skilled in the art.

Tablets and capsules for oral administration may be in unit dose form, and may contain excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavoring or coloring agents.

For topical application to the skin, the drug may be made up into a cream, lotion or ointment. Cream or ointment formulations that may be used for the drug are conventional formulations well known in the art. Topical administration includes transdermal formulations such as patches.

For topical application to the eye, the inhibitor may be made up into a solution or suspension in a suitable sterile aqueous or non-aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium, either subcutaneously, or intravenously, or intramuscularly, or intrasternally, or by infusion techniques, in the form of sterile injectable aqueous or oleaginous suspensions. Depending on the vehicle and concentration used, the drug can either be suspended or dissolved in the vehicle. Advantageously, adjuvants such as a local anaesthetic, preservative and buffering agents can be dissolved in the vehicle.

Pharmaceutical compositions may conveniently be presented in unit dosage form and may be prepared by any of the methods well known in the art of pharmacy. The term "unit dosage" or "unit dose" means a predetermined amount of the active ingredient sufficient to be effective for treating an indicated activity or condition. Making each type of pharmaceutical composition includes the step of bringing the active compound into association with a carrier and one or more optional accessory ingredients. In general, the formulations are prepared by uniformly and intimately bringing the active compound into association with a liquid or solid carrier and then, if necessary, shaping the product into the desired unit dosage form.

The antimicrobial compounds may also be administered in combination with an additional active agent, such as, for example, an inhibitor of bacterial efflux. Efflux pumps are proteins that unidirectionally remove antibiotics from cytoplasmic compartments, and are considered to be a mechanism of antibacterial resistance. Bacterial efflux inhibitors include chalcone compounds as disclosed in WO 11/075, 136, the polybasic compounds disclosed in WO 10/054,102, the quaternary alkyl ammonium functional compounds disclosed in WO 08/141,012, the compounds disclosed in WO 05/007162, the substituted polyamines of WO 04/062674, which are incorporated herein by reference in their entirety.

In another embodiment, the antimicrobial compounds of Formula I can be administered with a second antibiotic. Exemplary second antibiotics include, for example, glycopeptides (e.g, vancomycin or teicoplanin); penicillins, such as amdinocillin, ampicillin, amoxicillin, azlocillin, bacampicillin, benzathine penicillin G, carbenicillin, cloxacillin, cyclacillin, dicloxacillin, methicillin, mezlocillin, nafcillin, oxacillin, penicillin G, penicillin V, piperacillin, and ticarcillin; cephalosporins, such as cefadroxil, cefazolin, cephalexin, cephalothin, cephapirin, cephradine, cefaclor, cefamandole, cefonicid, cefmetazole, cefoxitin, and cefuroxime, cefoperazone, cefotaxime, cefotetan, ceftazidime, ceftizoxime, ceftriaxone, and moxalactam; carbapenems such as imipenem; monobactams such as aztreonam; tetracyclines such as demeclocycline, tigilcycline, doxycycline, methacycline, minocycline, and oxytetracycline; aminoglycosides such as amikacin, gentamicin, kanamycin, neomycin, netilmicin, paromomycin, spectinomycin, streptomycin, and tobramycin; polymyxins such as colistin, colistimathate, and polymyxin B, and erythromycins and lincomycins and also sulfonamides such as sulfacytine, sulfadiazine, sulfisoxazole, sulfamethoxazole, sulfamethizole, and sulfapyridine; trimethoprim, quinolones, novobiocin, pyrimethamine, rifampin, quinolines, fluoroquinolines; and combinations thereof.

The invention is further illustrated by the following non-limiting examples.

EXAMPLES

Materials and Methods

Bacterial strains and growth conditions. Organisms and strains used in this study and their genotypes are summarized in Table 1. Luria-Bertani (LB) media (10 g/L tryptone, 10 g/L NaCl, 5 g/L yeast extract, pH 7.2) was used to grow B. subtilis 168, S. aureus FRI100, and P. aeruginosa K1115 strains. For P. aeruginosa PAO1 and K1119 strains and two E. coli BW25113 strains, M8 minimal media (241 mg/L MgSO$_4$, 4 mg/L glucose, 5 mg/L casamino acids, 12.8 g/L Na$_2$HPO$_4$.7H$_2$O, 3 g/L KH$_2$PO$_4$, and 0.5 g/L NaCl) was used. PYE media (2 g/L peptone, 1 g/L yeast extract, 0.8 mM MgSO$_4$, and 0.5 mM CaCl$_2$) was used for culturing C. crescentus cells at 30° C. All cultures were grown at 37° C., except for C. crescentus (30° C.). All cultures were grown while shaking at 200 rpm.

TABLE 1

List of Strains

| Organism/Strain | Genotype/Description |
|---|---|
| C. crescentus CB15N | synchronizable derivative of wild-type CB15 |
| C. crescentus MT97 | CB15N mipZ-yfp |
| C. crescentus AM138 | Pxyl-venus-ftsA, kan$^R$ |
| S. aureus FRI 100 | sea$^+$ (Tmm$^s$ Hem$^{+a}$ Em$^s$) |
| E. coli BW25113 | Δ(araD-araB)567 ΔlacZ4787(::rrnB-3) lambda$^-$ rph-1 Δ(rhaD-rhaB)568 hsdR514 |
| E. coli BW25113 ΔtolC | BW25113 tolC::kan$^R$ |
| P. aeruginosa PAO1 | Prototroph |
| P. aeruginosa K1115 | ilv-220 thr-9001 leu-9001 met-9011 pur-67 aphA ΔmexCD-oprJ ΔmexAB-oprM |
| P. aeruginosa K1119 | PAO1 ΔmexAB-oprM |
| B. subtilis 168 | trpC2 |
| B. subtilis DS4294 | amyE::Pxyl-gfp-minD, cat$^R$ |
| Salmonella typhimurium | Clinical isolates from the Department of Medical Microbiology and Immunology (MMI) at the University of Wisconsin-Madison |
| Vibrio cholerae | Clinical isolates from the Department of Medical Microbiology and Immunology (MMI) at the University of Wisconsin-Madison |
| Shigella boydii | Clinical isolates from the Department of Medical Microbiology and Immunology (MMI) at the University of Wisconsin-Madison |
| Morganella morganii | Clinical isolates from the Department of Medical Microbiology and Immunology (MMI) at the University of Wisconsin-Madison |
| Edwardsiella tarda | Clinical isolates from the Department of Medical Microbiology and Immunology (MMI) at the University of Wisconsin-Madison |
| Acinetobacter baumannii | Clinical isolates from the Department of Medical Microbiology and Immunology (MMI) at the University of Wisconsin-Madison |
| Enterobacter aerogenes | Clinical isolates from the Department of Medical Microbiology and Immunology (MMI) at the University of Wisconsin-Madison |
| Klebsiella pneumoniae | Clinical isolates from the Department of Medical Microbiology and Immunology (MMI) at the University of Wisconsin-Madison |

In vivo screen with a Caulobacter crescentus strain that expresses MipZ-YFP. Hits from in vitro screens were tested for activity in vivo. A C. crescentus strain (MT97) that expresses mipZ-yfp from the native mipZ promoter was used. An overnight culture of MT97 was diluted to an absorbance ($\lambda$=600 nm) of ~0.1; the diluted culture was grown further for at least 1 hour prior to compound treatment. Compounds were mixed with a solution of 1% agarose in M2G media to achieve a final concentration of 20 μM. The cells (1 μL per pad) were transferred on top of the compound-containing agarose pad, and the cell morphology and localization of MipZ-YFP were imaged for a period of 24 hours using epifluorescence microscopy. In between microscopic observations, the inoculated pads were incubated at 30° C. to promote growth.

Effects of compounds on MipZ localization. A strain of C. crescentus in which MipZ was translationally fused to yellow fluorescent protein (YFP) was used to determine the effect of DCAP on MipZ localization. For experiments with C. crescentus expressing MipZ-YFP, overnight cultures were diluted 10-fold and incubated at least 1 hour prior to treatment with compounds. After adding compounds, cells were incubated at 200 rpm and 30° C. for 20 minutes. Cells were imaged as described above. Following cell segmentation and fluorescence signal calculation in MicrobeTracker, a separate MATLAB script was used to detect signal peaks within an individual cell. The number of total peaks and peak locations were calculated (i.e., poles or mid-cell) for each cell. Poles were defined as 1-25% and 75-100% along the normalized cell length (1-100%). Cells were classified as 'wildtype' if their catalogued information agreed with one of the following criteria: 1) MipZ-YFP was unipolar, meaning there was one peak and the peak resides within a pole region; and 2) MipZ-YFP was bipolar, meaning there were two peaks and both peaks are within a polar region. After this classification, a contingency table was created with the total number of cells analyzed, and the number of cells with the 'wildtype' localization. Using the GraphPad InStat program, the Fisher's exact test was applied to calculate two-sided p-values between DMSO and compound-treated cells.

Figure 5:
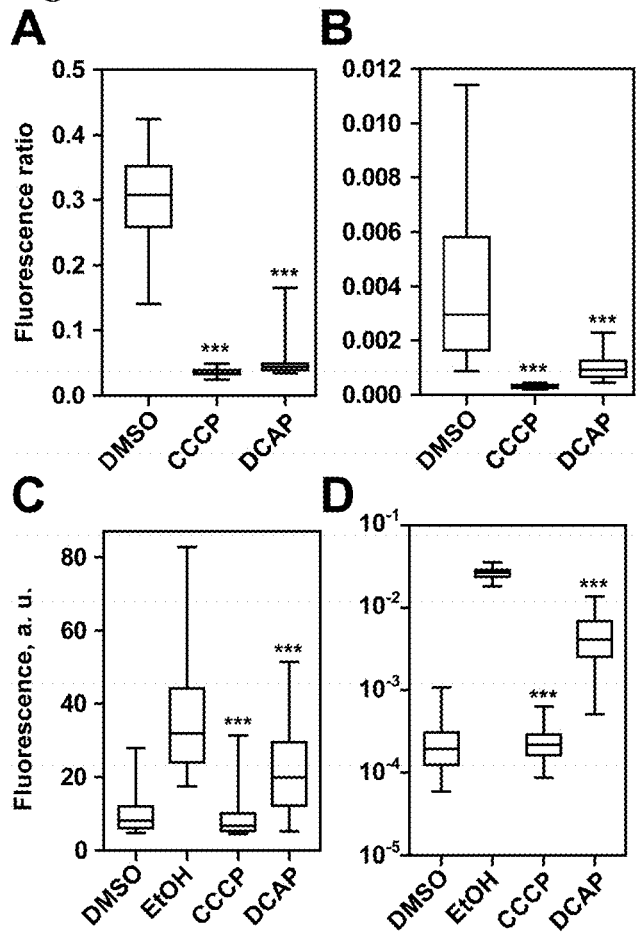
FIG. 5: (A, B) Measurement of ΔΨ using $DiOC_2$ A) Data for *B. subtilis* (n≤8,964 cells). B) Data for *C. crescentus* (n≥158 cells). C) Measurement of *B. subtilis* membrane permeability using PI (n≥2,546 cells). D) Measurement of *C. crescentus* membrane permeability using PI (n≥35 cells). In box plots, the top whisker represents 95%, the bottom whisker is 5%, the top of the box is 75%, the bottom of the box is 25%, and the line inside the box indicates the median of each sample population. Three asterisks (***) refers to p<0.001.

Fluorescence microscopy and flow cytometry to measure $\Delta\Psi$. The fluorescent probe, 3,3'-diethyloxacarbocyanine iodide ($DiOC_2$) was used to measure $\Delta\Psi$ in DMSO and in compound-treated cells. To eliminate the possibility of an interaction between the probe and compounds, the fluorescence intensity of solutions of $DiOC_2$ was measured in the presence and absence of the compounds as described in the art. To measure $\Delta\Psi$ in B. subtilis cells, flow cytometry was used. Cell suspensions were labeled with 30 µM $DiOC_2$ and filtered through a Nylon filter containing 60-µm diameter pores. The fluorescence of these cells was measured using a BD LSR II flow cytometer. The following instrument settings were used for detection: low flow rate, 488 nm excitation laser, 530/30 nm emission filter for green fluorescence, and 575/26 nm emission filter for red fluorescence. FlowJo software was used to analyze flow cytometry data. First, a gate was drawn around the region where cells were detected in the forward versus side scatter area plot. Gating enabled the exclusion of any non-cellular materials in the sample that the instrument detected. The ratio of red-to-green fluorescence was calculated for each particle within the gate using the software, and the resulting data was exported to GraphPad Prism to create box plots shown in FIG. 5. Statistical parameters were calculated using the Kruskal-Wallis non-parametric one-way analysis of variation (GraphPad InStat).

For experiments with C. crescentus cells, the cells were prepared by diluting the overnight culture 10-fold into fresh PYE medium. The diluted culture was grown for 1 hour at 200 rpm and 30° C. The cells were treated with compounds for 10 minutes at room temperature, $DiOC_2$ dye was added to a final concentration of 30 µM, and incubated for 10 minutes. After labeling, small aliquots (1-2 µl) of the suspensions of cells were transferred onto 1% agarose pads for fluorescence microscopy. A Nikon Eclipse TE2000E inverted microscope with an Andor DU-895 EMCCD camera, a Perfect Focus system, and an encoded z-stage were used for phase contrast and epifluorescence microscopy. For detecting green and red fluorescence of the dye, the following wavelengths ($\lambda_{ex}/\lambda_{em}$): 484/520 nm and 555/620 nm, respectively, were used. Acquired images were analyzed using the MATLAB-based script MicrobeTracker. Using this software, the area of individual cells in the phase contrast images was segmented. The segmentation was applied to the fluorescence images to calculate the fluorescence intensity for individual cells. A separate MATLAB script was written to process the results from MicrobeTracker, in which the cell-area normalized ratio of red to green fluorescence for each cell was calculated. This data was exported to GraphPad Prism and GraphPad InStat for creating box plots and performing statistical analysis (one-way analysis of variation), respectively.

Measurement of membrane permeability using fluorescence microscopy and flow cytometry. The DNA-binding probe, propidium iodide (PI) was used to measure the relative membrane permeability between DMSO, ethanol (50% v/v for C. crescentus and 70% v/v for B. subtilis) and compound-treated cells. To eliminate the possibility of an interaction between the fluorophore and small molecules, the fluorescence intensity of solutions of PI was measured in the presence and absence of the compounds. For experiments with B. subtilis cells, flow cytometry was used as described in the previous section, except the fluorescence settings in the instrument were as follows: 488 nm excitation laser, 610/20 nm emission filter. When using FlowJo to analyze the data, the auto-fluorescence from cells was excluded from PI fluorescence. Other details for the analysis are identical to the description in the previous section.

For experiments with C. crescentus cells, the cells were prepared by diluting the overnight culture 10-fold into fresh PYE medium. The diluted culture was grown for 1-3 hours at 200 rpm and 30° C. The cells were treated with compounds for 10 minutes at room temperature, PI was added at a final concentration of 20 µM, and incubated for 10 minutes. Image acquisition and data analysis were performed as described in the previous section.

Measurement of compound effects on FtsA: For experiments with C. crescentus expressing Venus-FtsA, a synchronized population of cells was used. First, an overnight culture was grown with kanamycin (5 µg/mL) and glucose (0.02% w/v). The presence of glucose suppressed the transcription of venus-ftsA from its xylose-inducible promoter. 2 mL of this culture was diluted into 25 mL of fresh PYE with the antibiotic and glucose, and incubated further to achieve an absorbance of ~0.6 ($\lambda$=600 nm). Once the cells reached mid-exponential phase, the culture was centrifuged for 10 minutes at 6000 rpm and 4° C. The cell pellet was resuspended in ice-cold M2 (a final volume of approximately 1000 µL) and 750 µL of this suspension was added to an equal-volume of sterile Percol (Sigma Aldrich). After thoroughly mixing the solution, it was centrifuged for 20 minutes at 11,000 rpm and 4° C. Upon centrifugation, the bottom band (swarmer cells) was taken and the cells were washed in ice-chilled M2 solution (1 mL). The washed cell pellet was suspended in fresh PYE containing kanamycin (no glucose, 6 mL). The cell suspension was incubated for 20 minutes and then xylose (0.03% w/v) was added to induce the expression of venus-ftsA. Cells were grown for another 20 minutes and subsequently treated with compounds. The cells were incubated for 20 minutes again in the presence of the compounds prior to imaging. Thus, the total time of xylose induction was 40 minutes, and the total time of compound treatment was 20 minutes. At this time point (60 minutes post synchrony), the majority of the cells were at the beginning of cell division. Imaging conditions and data analysis were identical to the conditions described for MipZ-YFP, except for a set of criteria used for defining 'wildtype' protein localization. 'Wildtype' was defined as 1) Venus-FtsA is unipolar, meaning there was one peak, and the peak resided within a polar region; and 2) Venus-FtsA was at the mid-cell, meaning there was one peak and it was within the mid-cell region (40-60% of the normalized cell length).

Measurement of compound effects on MinD: *B. subtilis* DS4294 (amyE::Pxyl-GFP-minD cat) cells were grown to exponential phase (λ=600 nm, 0.4-0.7) in LB with incubation at 30° C. and 200 rpm shaking. Cells were induced for GFP-MinD production by adding xylose to the media to a final concentration of 0.1% (w/v) followed by incubating for 75 min. After induction, cells were treated with compounds for 20 minutes before imaging. Other details for imaging conditions and data analysis were identical to those described for MipZ-YFP, except for the definition of poles, and a set of criteria used for defining 'wildtype' protein localization. 'Wildtype' was defined as 1) GFP-MinD was bipolar, meaning there were two peaks, and both peaks were at the poles (1-20% and 80-100% of the normalized cell length); 2) GFP-MinD was at the mid-cell in addition to the bipolar localization, meaning there were three peaks with two of them at the poles and one at mid-cell; and 3) GFP-MinD was at an quaternary position (20-40% and 60-80% of the normalized cell length) in addition to the bipolar and mid-cell localization (the total number of peaks was 4 if there is one quaternary peak, and the total was 5 if there are two quaternary peaks). Because *B. subtilis* cells can initiate division prior to finishing an earlier division and the completion of septation, these normal cells have peaks at quaternary positions. Any cells that did not fit these criteria were categorized as non-wildtype.

Determination of the minimum inhibitory concentration (MIC) of bacterial growth. The MIC of various organisms in liquid media was determined using the macrodilution method according to the NCCLS guidelines. For the starting inoculum, cultures were diluted to contain approximately $5 \times 10^5$ cells/mL in growth media. To create a two-fold dilution series for the macrodilution technique, each compound was added to the first culture tube (4 mL total volume) at the highest concentration. 2 mL of this culture was diluted into an equal volume of inoculated media (a two-fold dilution). The final volume for each culture was 2 mL. The MIC was determined by identifying the lowest concentration of compound that completely inhibited growth by visual inspection.

Determination of the Minimum Stationary-Bactericidal Concentration.

Cultures of *C. crescentus* (24 hour incubation) and *S. aureus* cells (5 day incubation) were grown from single colonies. Cells were collected by centrifugation (8500 rpm for 2.5 minutes) and re-suspended in M2 salt solution (for *C. crescentus*; 1.74 g/L $Na_2HPO_4$, 1.06 g/L $KH_2PO_4$, and 0.5 g/L $NH_4Cl$) or phosphate-buffered saline (for *S. aureus*; PBS, Fisher Scientific). The centrifugation and re-suspension was repeated two more times. After the repeated washing steps, the cell suspension was diluted 10-fold to achieve approximately $10^8$ cells/mL. Aliquots of the diluted cell suspension were transferred into wells of a 96-well plate (100 μL/well), and 2-fold serial dilutions were performed to test a range of antibiotic concentrations. The plate was sealed with Parafilm® and incubated for 24 hours at room temperature in the dark. After incubation, 50 μl was removed from each well to spread on nutrient agar plates (1.5% agar in PYE for *C. crescentus*, and LB for *S. aureus*). The colonies on each plate were counted after growing the cells for 1-2 days. For determining the kinetics of bactericidal activity of DCAP on stationary cultures, the washed cells were diluted by 100-fold in appropriate solutions and tested using a single concentration of the compound while including a DMSO control sample. Cell suspensions were kept in closed microcentrifuge tubes instead of the wells of 96-well plates. 100 μL of the suspensions was removed for plating at each time point. All MSC experiments were performed in static conditions.

Determination of the minimum biofilm inhibitory concentration of growth (bMIC) and biofilm eradication concentration (MBEC). Overnight cultures of *C. crescentus* and *S. aureus* were grown and diluted 100-fold into appropriate nutrient media. Aliquots of the diluted suspension were transferred into wells of 96-well plates (150 μL/well). 2-fold serial dilutions were performed for compound-containing wells. For every experiment, three replicates for each compound concentration tested were included. After transferring aliquots of the suspension, the plates were closed with specialized lids that have protruding pins (Nunc STP System), and the plates were sealed using Parafilm®. The plates were incubated in a static incubator at 30° C. (*C. crescentus*) or 37° C. (*S. aureus*) for 24 hours. After the cells had formed biofilms on the surface of the pins, the pins were rinsed by dipping them in M2 (*C. crescentus*) or PBS (*S. aureus*) solutions. To rinse the pins, clean, sterile 96-well plates were used (aliquots of 200 μL/well); each rinse lasted 10 sec. After washing away planktonic cells loosely bound to biofilms, the pins were inserted into a 96-well plate that was pre-aliquoted with nutrient media containing antibiotics (2-fold dilutions, a final volume of 150 μL/well). The plates were sealed with Parafilm®, and incubated for 17 hours, and the bMIC was measured at the end of the incubation by visual inspection. After the bMIC run, the rinse steps were repeated to remove planktonic cells, and the pins were inserted into a 96-well plate that was pre-aliquoted with drug-free nutrient media (aliquots of 150 μL/well). The plates were sealed with Parafilm®, incubated for 24 hours, and the MBEC was measured at the end of the incubation by visual inspection.

Rabbit red blood cell (RBC) hemolysis assay. Rabbit RBCs from Lampire Biological Laboratories were used. Prior to preparing the RBCs, compound-containing PBS solutions were serially diluted into a 96-well plate (a final volume of 100 μL/well). The RBC lysis solution (Epicentre Biotechnology) was included as a positive control for hemolysis. For each assay, 1 mL of the RBC suspension was removed from the stock bottle and centrifuged for 2 minutes at 2000 rpm. The pelleted cells were resuspended in sterile PBS solution and centrifuged again. The cells were resuspended in PBS and diluted 5-fold into the same solution. 100 μL aliquots of RBCs were added into wells of a 96-well plate that contained an equal volume of a solution of compound in PBS. The plates were incubated for varying amounts of time depending on the microbial assay conditions to be emulated. For MIC-like conditions, plates were incubated for at least 17 hours at 30° C. or 37° C. For MSC-like conditions, the incubation time was either 2 hours or 6 hours at 30° C. or 37° C. During the incubation, un-lysed RBCs settled at the bottom of the wells. At the end of the incubation, 90 μL of the supernatant was transferred into the wells of a fresh 96-well plate, and the absorbance of the heme at $\lambda=405$ nm was measured.

Example 1: Selection of Compounds

Figure 2:
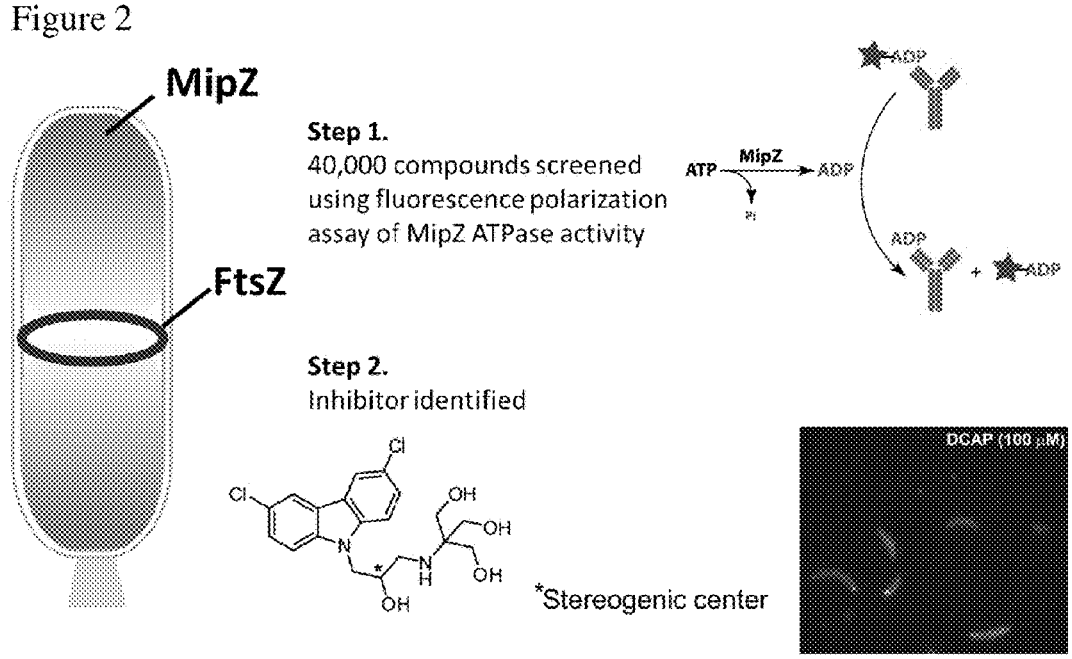
FIG. 2 is a schematic of the assay used to identify inhibitors of MipZ.

In *Caulobacter crescentus* cells, the mechanism of accurately placing FtsZ in time and space in the cell involves an ATPase, MipZ. (FIG. 1) The ATP-bound form of MipZ promotes depolymerization of FtsZ filaments by increasing the GTP hydrolysis rate of FtsZ. In addition to its inhibition of FtsZ, MipZ binds to nucleoproteins near the origin of the chromosome and establishes an asymmetric polar gradient. The gradient becomes bipolar (i.e., symmetric) when the cell undergoes chromosome replication to place two origins at opposite poles. This bipolar gradient of MipZ positions the division at the mid-cell: FtsZ is localized at the mid-cell, where the concentration of the inhibitory gradient of MipZ is the lowest. Thus, MipZ coordinates chromosome segregation and the onset of cell division both spatially and temporally such that FtsZ assembles at the mid-cell after the segregation of the chromosomes. Because of the relationship between FtsZ and MipZ, a coupling assay and a fluorescence polarization assay of MipZ ATPase activity were used to screen compounds for their ability to inhibit cell division. (FIG. 2)

In vitro ATPase screen with purified recombinant MipZ. Recombinant MipZ for in vitro screens was prepared as described in the art (Thanbichler, M.; Shapiro, L. Cell 2006, 126, 147.). Two ATPase assays were used to screen three small molecule libraries (a total of 43,400 compounds) at the University of Wisconsin Carbone Cancer Center. One assay utilized pyruvate kinase and lactic dehydrogenase as coupling enzymes, and phosphoenolpyruvate and NADH as their substrates, respectively. A solution of coupling enzymes, their substrates, Triton X-100 and MipZ were aliquoted (22.3 µL, per well) in 384-well black plates using Biomek FX liquid handler (Beckman Colter). Plates were briefly centrifuged to pull liquids to the bottom of the wells. Pin tools were used to deliver 0.2 µL, of a stock solution of unique small molecules (10 mM in DMSO) from chemical libraries to each well. The first two columns of each plate were reserved for controls and did not receive compounds from the libraries. A solution of ATP (2.5 µL, per well) was added using a Biotek Fill instrument to all wells except the first column for each plate to initiate ATP hydrolysis. Final concentrations of assay components were: 0.01% Triton X-100, 1 mM phosphoenolpyruvate, 0.3 mM NADH, 3 U/mL pyruvate kinase, 3 U/mL lactic dehydrogenase, 7.5 µM MipZ, and 1 mM ATP in a buffered solution of 50 mM Tris-HCl, 50 mM KCl, and 10 mM $MgCl_2$. The plates were gently vortexed to mix the solution and incubated for 3 hours at 30° C. After incubation, the fluorescence emission from NADH was measured using a Tecan Safire II® plate reader ($\lambda_{ex}$=340/35 nm; $\lambda_{em}$=460/10 nm). Measurements of the fluorescence intensity from control wells were used to calculate the Z-factor; the minimum Z-factor for all plates was 0.7. The coupling enzyme assay was used to screen compounds from Maybridge and Life Chemicals libraries. Compounds that inhibited ≥60% of ATP hydrolysis compared to the positive control were identified as hits and were screened using a secondary assay to eliminate compounds that target coupling enzymes. The secondary assay consisted of the same reaction components as the primary assay, except for the omission of MipZ and ATP. A solution of ADP was added instead. The fluorescence emission of compounds that did not inhibit coupling enzymes was measured at the specified wavelengths used for NADH, and the compounds were retested for their inhibitory effect on MipZ activity in vitro.

In addition to the coupling enzyme assay, a fluorescence polarization (FP) assay was used to monitor the ATPase activity of MipZ in vitro. Reaction conditions and component concentrations were the same as the coupling enzyme assay unless noted otherwise. The FP assay utilized anti-ADP antibodies and Alexa633-labeled ADP. A Transcreener® $ADP^2$ FP assay kit from BellBrook Labs (Madison, Wis.) was used. A solution of MipZ was aliquoted (10 µL per well) into plates, and addition of ATP (1 µL of 5 mM stock solution per well) initiated the reaction. After 3 hours, 10 µL of ADP detection mix (541 µg/mL of antibody) was added to each well, and the plates were incubated for 1 hour at 25° C. The following wavelengths were used for FP measurements: 635 nm for excitation and 670/20 nm for emission. The Z-factor for the FP assay was ≥0.7. The FP assay was used for screening compounds from the Life Chemicals library and the Spectrum Collection. Hits from the FP assay were tested for inhibition of the anti-ADP antibody by repeating the assay in the absence of MipZ, and checked for their intrinsic fluorescence at the specified wavelengths used for the Alexa633 probe.

Hits were further screened for antibacterial activity using a *Caulobacter crecentus* strain that expresses MipZ-YFP as described in Materials and Methods. DCAP was confirmed as having antibacterial activity in the MipZ-YFP assay (data not shown).

(2-((3-(3,6-dichloro-9H-carbazol-9-yl)-2-hydroxypropyl)amino)-2-(hydroxymethyl)propane-1,3-diol) (DCAP) was identified in the screen.

Example 2: Confirmation of the DCAP Structure

The identification of (2-((3-(3,6-dichloro-9H-carbazol-9-yl)-2-hydroxypropyl)amino)-2-(hydroxymethyl)propane-1,3-diol) (DCAP) was confirmed by nuclear magnetic resonance (NMR) spectroscopy and high resolution electrospray ionization. DCAP used in all experiments was purchased from Ryan Scientific (catalog number F3255-0148, Mt. Pleasant, S.C.). A Varian MercuryPlus 300 MHz instrument (Magnetic Resonance Facility in the Chemistry Department of the University of Wisconsin-Madison) was used to obtain 1D $^1$H and $^{13}$C NMR spectra for DCAP at 25° C. A Bruker Avance III 500 MHz instrument (National Magnetic Resonance Facility at Madison) was used to collect 2D $^{13}$C-HMBC, $^{15}$N-HMBC, HSQC, COSY, and TOCSY spectra for DCAP structure verification. The solvent used was deuterated dimethyl sulfoxide. The data were analyzed using Sparky (T. D. Goddard and D. G. Kneller, University of California, San Francisco) and NUTS (Acorn NMR). The NMR data is summarized below:

$^1$H NMR spectrum. $^1$H NMR (299.7 MHz, DMSO) δ 8.30 (d, J=2.1 Hz, 2H), 7.68 (d, J=8.8 Hz, 2H), 7.47 (dd, J=8.8, 2.2 Hz, 2H), 4.99 (s, 1H), 4.44 (dd, J=14.8, 4.0 Hz, 2H), 4.27 (m, 3H), 3.87 (s, 1H), 3.34 (s, 6H), 2.67 (m, 2H), 1.81 (s, 1H).

$^{13}$C NMR spectrum. $^{13}$C NMR (75.4 MHz, DMSO) δ 139.6, 126.0, 123.4, 122.4, 120.1, 111.9, 70.0, 61.2, 59.4, 47.6, 45.1

DCAP was also analyzed using high resolution electrospray ionization mass spectrometry in positive ion mode to determine the exact mass of the compound (Mass Spectrometry Facility, Department of Chemistry at the University of Wisconsin-Madison). Expected masses were $(M+H)^+$=413.0952 and $(M+Na)^+$=435.0849. Measured mass was 435.0832 (Data not shown).

Figure 3:
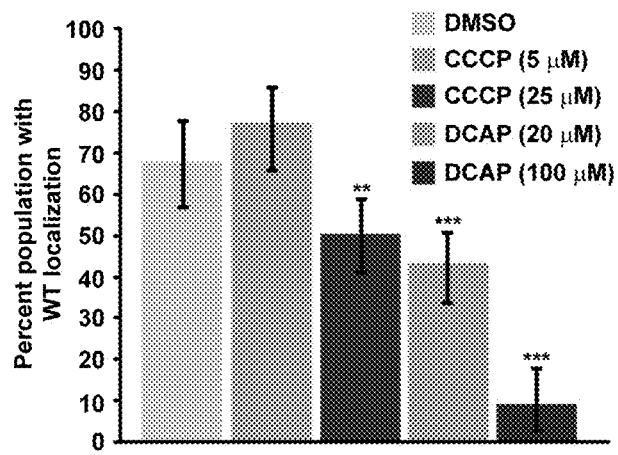
FIG. 3 shows an analysis of MipZ-YFP localization. (A) Plot of percent of population with wild type localization for treatment with different compounds at different concentrations. (B) Representative fluorescence images of *C. crescentus* cells expressing MipZ-YFP.
Figure 3:
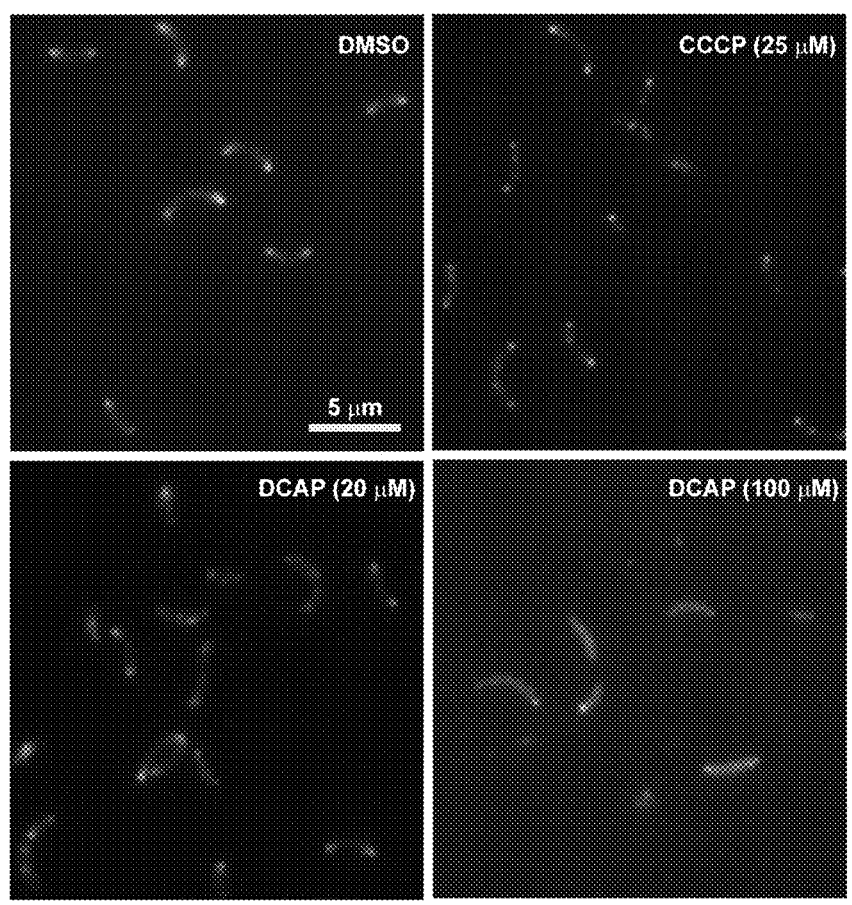

Example 3: Determination of MipZ Localization in *C. Crescentus* in the Presence of DCAP Using a strain of *C. crescentus* in which MipZ was translationally fused to yellow fluorescent protein (YFP), it was found that the treatment of cells with DCAP (20 µM)

caused MipZ-YFP to mislocalize (FIG. 3). As a positive control, carbonyl cyanide m-chlorophenyl hydrazone (CCCP) was used. In FIG. 3, 'wildtype' (WT) localization was defined as 1) unipolar (a single peak of fluorescence signal at a pole) and 2) bipolar (two peaks at poles). All images were acquired 20 min after treating cells with compounds. At least 69 cells were analyzed for each sample. Two-sided p-values using Fisher's exact test in comparison to DMSO: p=0.0075 () for 25 µM of CCCP, p=0.0002 (*) for 20 µM of DCAP, and p<0.0001 (***) for 100 µM of DCAP.

Figure 4:
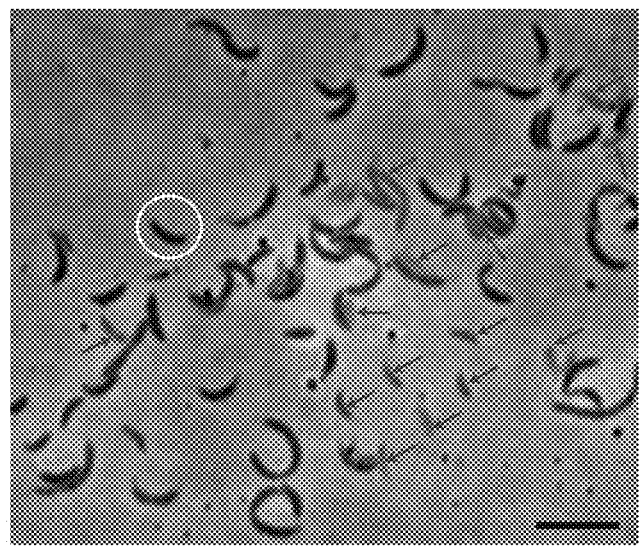
FIG. 4 shows *C. crescentus* cells 20 minutes after treatment with DCAP (100 µM). Cell lysis was observed in the population (cells with arrows). The lysed cells appear fainter in phase contrast images, compared to un-lysed cells (e.g., a cell in the white circle).

At high concentrations of DCAP (≥75 µM), cell lysis within minutes after treatment was observed (FIG. 4). This observation suggested to us that DCAP may not specifically inhibit MipZ in the cell but instead alter the properties of the cell envelope.

Example 4: Effect of DCAP on Membrane Potential

To test the hypothesis that DCAP alters the properties of the cell envelope, the membrane potential in the presence and absence of DCAP was measured.

$\Delta\Psi$ was measured for two model bacteria, C. crescentus (Gram-negative) and Bacillus subtilis (Gram-positive), in the absence and presence of DCAP. As a positive control, carbonyl cyanide m-chlorophenyl hydrazone (CCCP) was used. CCCP increases the permeability of protons across the membrane and decreases $\Delta\Psi$. To visualize changes in the membrane potential, the fluorescent probe 3,3'-diethyloxacarbocyanine iodide ($DiOC_2$) was used. $DiOC_2$ emits green fluorescence ($\lambda$=530 nm) in its monomeric form. Its fluorescence emission maximum is red-shifted ($\lambda$=576 nm) upon self-association. A large $\Delta\Psi$ stimulates the aggregation of $DiOC_2$ and produces a high ratio of $\lambda_{576}/\lambda_{530}$. Conversely, $\lambda_{576}/\lambda_{530}$ decreases when $\Delta\Psi$ is dissipated in bacteria. FIGS. 5A and B illustrate $\lambda_{576}/\lambda_{530}$ for cells treated with DMSO, CCCP, and DCAP. A significant decrease in $\lambda_{576}/\lambda_{530}$ was apparent after 20 minutes of treatment with CCCP and DCAP (p<0.001) and indicated that the $\Delta\Psi$ was dissipated rapidly. Antibiotics that do not target the bacterial membrane can decrease the potential over a long period of exposure (e.g. 3-4 hours); however, the rapid action of DCAP suggests that the dissipation in $\Delta\Psi$ was due to its direct effect on the membrane.

Example 5: Effect of DCAP on Membrane Permeability

The mechanism of action of DCAP was explored. One possibility is that DCAP functions as an ionophore similar to CCCP. Alternatively, DCAP may increase the general permeability of the membrane. To investigate the mechanism, propidium iodide (PI) was used to label the DNA of cells with compromised membranes. As shown in FIGS. 5C and D, ethanol-treated cells were intensely labeled with PI, while the DMSO control sample was not. Treating cells with CCCP did not increase DNA labeling with PI; the fluorescence emission of these cells was similar to the DMSO sample. Addition of DCAP to cells increased the fluorescence of cells labeled with PI, although the intensity was significantly lower than the ethanol-treated cells (P<0.001). These results suggest that DCAP has at least two mechanisms of antimicrobial action: it decreases $\Delta\Psi$ by facilitating ion transport across the membrane and has a minor effect on the general permeability of the lipid bilayer.

Figure 6:
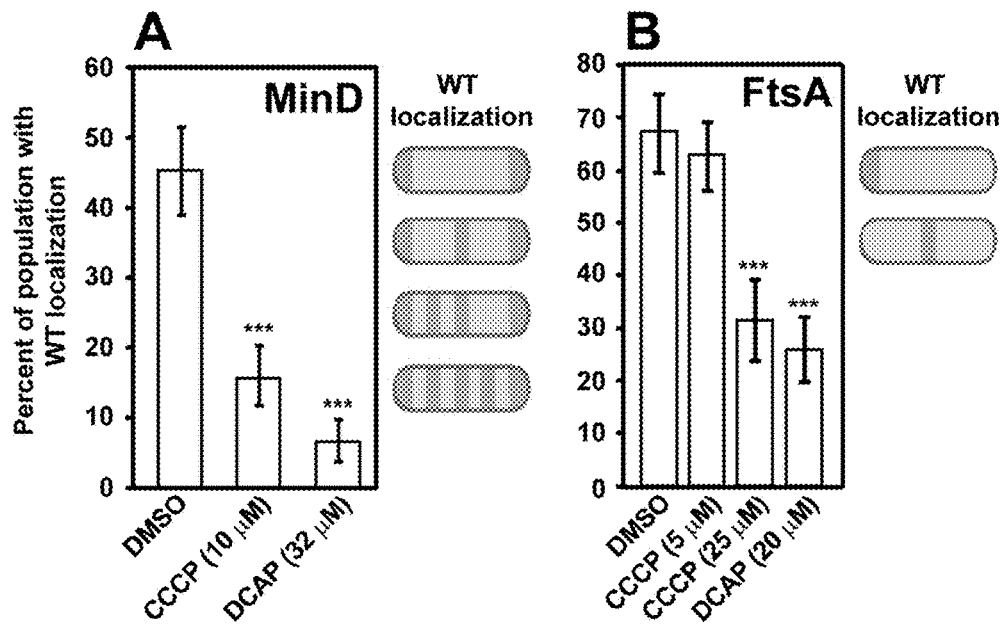
FIG. 6 shows an analysis of membrane protein localization in cells that express fluorescent fusion proteins (p<0.0001=***, compared to DMSO). Wildtype (WT) localizations depicted in green in a cartoon cell are shown for each protein. A) Analysis of GFP-MinD in *B. subtilis* (n≥252 cells). B) Analysis of Venus-FtsA in *C. crescentus* (n≥150 cells). Error bars represent the 95% confidence interval of percentages reported.
Figure 7:
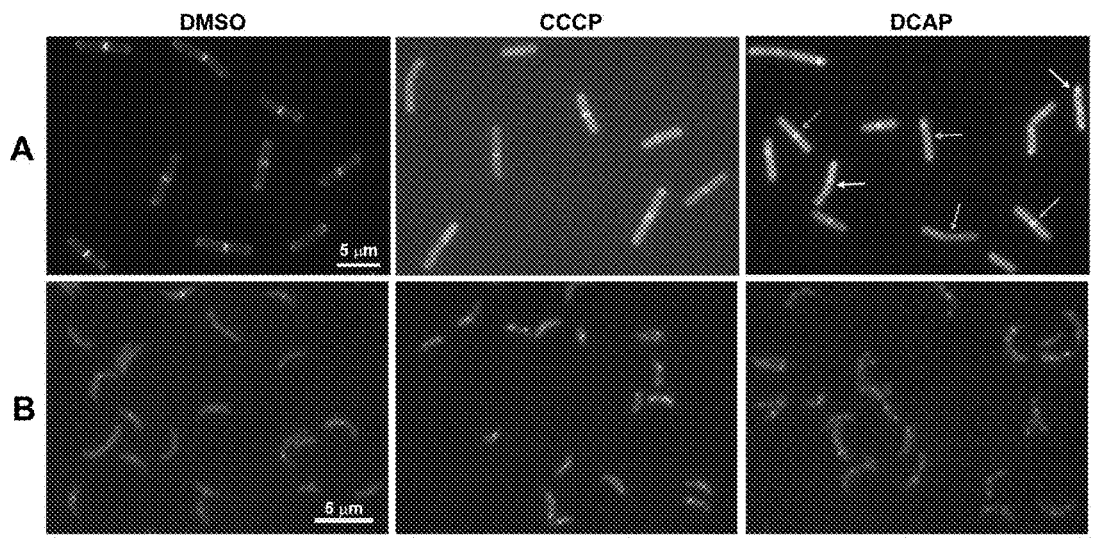
FIG. 7 shows representative fluorescence images of cells treated with DMSO, CCCP or DCAP for 20 minutes. (A) *B. subtilis* cells expressing GFP-MinD. The DCAP image shows cells with peaks mislocalized to random locations in the cell (orange arrows), cells in which the number of fluorescent peaks increased significantly (white arrows), and cells with diffused fluorescence signal throughout the cell and no polar localizations (blue arrows). (B) *C. crescentus* cells expressing Venus-FtsA.

Example 6: Effect of DCAP on In Vivo Localization of Division Proteins MinD and FtsA $\Delta\Psi$ was recently identified as an important parameter for the in vivo localization of division proteins associated with the bacterial membrane, including MinD and FtsA. The treatment of B. subtilis cells with either CCCP or DCAP altered the localization of a fusion of green fluorescent protein to MinD (GFP-MinD) compared to DMSO-treated cells (FIG. 6A). MinD localizes to the poles of B. subtilis cells and guides division plane formation at the mid-cell. As division progresses, MinD accumulates at the mid-cell and marks the sites of future cell poles. Treating B. subtilis cells expressing GFP-MinD with CCCP led to more diffuse fluorescence throughout the cell but had little effect on the location of the signal compared to the DMSO control (FIG. 7A). In DCAP-treated cells, GFP-MinD mislocalized—the number of fluorescent foci increased in some cells while in others the fluorescence signal became more diffuse and was no longer concentrated at the poles (FIG. 7A).

In addition to perturbing the localization of MinD in B. subtilis, CCCP and DCAP influenced the distribution of FtsA in C. crescentus. FtsA is a peripheral membrane protein that interacts with FtsZ and activates the recruitment of downstream division proteins. FtsA resides at one pole (i.e., the pole opposite to the stalk) in non-dividing C. crescentus cells and is recruited to the mid-cell as division begins. To study cells at this stage of division, cells that express a fluorescent fusion of the protein, Venus-FtsA, were synchronized and then treated with CCCP and DCAP. Treatment of C. crescentus cells with CCCP at its minimum inhibitory concentration (5 µM) did not alter the localization of FtsA; however, a higher concentration of CCCP (25 µM) had a significant effect on the position of FtsA. Most cells treated with DCAP exhibited multiple peaks of FtsA fluorescence (≥2) instead of a single peak—either at the pole or mid-cell—observed in untreated cells (FIG. 7B). The observation that DCAP causes the mislocalization of membrane proteins in B. subtilis and C. crescentus is consistent with the hypothesis that the compound decreases $\Delta\Psi$. The effect of DCAP was similar to the ionophore CCCP; however, DCAP causes more severe protein mislocalization at its MIC, which may arise from its influence on membrane permeability.

Example 7: Measurement of Minimum Inhibitory Concentrations of DCAP

After confirming the membrane-targeting activity of DCAP, the efficacy of DCAP against other bacterial species was tested. Table 2 demonstrates that DCAP inhibits the growth of Escherichia coli, Pseudomonas aeruginosa, and Staphylococcus aureus. Deleting one or more efflux pumps in E. coli and P. aeruginosa strains increased the sensitivity of cells to DCAP. Efflux pumps are active against a broad range of compounds and typically consist of three components: two transmembrane proteins, one in the inner and the other in the outer membrane, and a periplasmic protein that connects the two transmembrane components. Deleting to/C whose product is embedded in the outer membrane in E. coli strain BW25113 reduced the MIC of DCAP by 4-fold. This result suggests that the activity of DCAP in Gram-negative bacteria is largely due to its interaction with the inner membrane.

TABLE 2

Measurements of compound concentrations toxic to actively growing bacterial cells (ND, not determined).

| Organism/Strain | MIC | | |
|---|---|---|---|
| | DCAP (µM) | Amp (µg/mL) | CCCP (µM) |
| C. crescentus CB15N | 15 | 50 | 5 |
| S. aureus FRI 100 | 50 | 0.125 | 1.25 |
| E. coli BW25113 | 80 | ND | ND |
| E. coli BW25113 ΔtolC | 20 | ND | ND |
| P. aeruginosa PAO1 | 160 | ND | ND |
| P. aeruginosa K1115 | 80 | ND | ND |
| P. aeruginosa K1119 | 160 | ND | ND |
| B. subtilis 168 | 32 | ND | 10 |
| S. typhimurium | 50 | ND | ND |
| V cholera | 100 | ND | ND |
| S. boydii | 100 | ND | ND |
| M. morganii | 200 | ND | ND |
| E. tarda | 200 | ND | ND |
| A. baumannii | 200 | ND | ND |
| E. aerogenes | 200 | ND | ND |
| K. pneumoniae | 100 | ND | ND |

TABLE 3

Measurements of compound concentrations toxic to stationary bacterial cells

| Organism/Strain | MSC | | | bMIC | | | MBEC | | |
|---|---|---|---|---|---|---|---|---|---|
| | DCAP (µM) | Amp (µg/mL) | CCCP (µM) | DCAP (µM) | Amp (µg/mL) | CCCP (µM) | DCAP (µM) | Amp (µg/mL) | CCCP (µM) |
| C. crescentus CB15N | 20 | >400 | 2.5 | 20 | 100 | 5 | 40 | >400 | 5 |
| S. aureus FRI 100 | 75 | 100 | >400 | 100 | 0.8 | 2.5 | >200 | >200 | 80 |

In addition to its activity against actively growing bacteria, DCAP kills cells in stationary phase (Table 3). This property was tested against C. crescentus and S. aureus. S. aureus was used as a model Gram-positive bacterium rather than B. subtilis for these experiments, as B. subtilis can sporulate under starvation conditions and does not form robust biofilms on the plastic surfaces used as substrates. To ensure that bacteria were deprived of nutrients, the cells were grown into late stationary phase (i.e., 24 hours for C. crescentus and 5 days for S. aureus). These cells were collected, suspended in isotonic solutions devoid of amino acids or sugars, and treated with a small molecule (DMSO, DCAP, CCCP or ampicillin). Cell viability was measured over time by plating culture aliquots on non-selective, solid growth media. The minimum concentration of antibiotic required to completely eliminate colony formation was designated as the minimum stationary-bactericidal concentration (MSC). The MSC and MIC of DCAP for each organism were similar while the efficacy of ampicillin was significantly reduced for stationary cells of both organisms (Table 3). The MSC of ampicillin for S. aureus was 1000-fold higher than its MIC, while the MSC of ampicillin for C. crescentus was beyond the range of the measurements. CCCP inhibited the proliferation of C. crescentus cells regardless of their physiological status. However, the MSC of CCCP for S. aureus was >300-fold higher than the MIC. This dramatic decrease in the effectiveness of CCCP in S. aureus may be due to changes in membrane composition as cells adjust their metabolism in nutrient-deprived conditions. Overall, CCCP and DCAP were more effective in killing stationary cells than ampicillin.

Membrane-active compounds are also efficient at eradicating biofilm-associated cells (Table 2). Biofilms are implicated in a wide range of human diseases including cystic fibrosis and urinary tract infection and are particularly recalcitrant to antibiotics. The heterogeneity in the physiology of cells in biofilms makes it possible for the bacterial communities to persist in stressful conditions. To determine the efficacy of antibiotics against biofilms, the minimum biofilm inhibitory concentration (bMIC) and the minimum biofilm eradication concentration (MBEC) were measured. Briefly, cell suspensions from overnight cultures were diluted and transferred into the wells of a 96-well plate; the lid of the plate contained 96 individual plastic pins that protruded into each of the 96 wells. Biofilms formed on the surface of the pins after incubation for 24 hours and were transferred to growth media and serially dosed with DCAP, CCCP, or ampicillin. After 24 hours of exposure to compounds, the lowest concentration of antibiotic that inhibited planktonic cell growth in the wells (bMIC) was determined. Since bMIC is a measurement of the rapid growth of freely suspended cells released from biofilms in the presence of antibiotics, the bMIC and MIC values did not differ significantly (Table 2).

After performing bMIC experiments, biofilms growing on the pins of the lid were transferred to nutrient media devoid of antibiotics to measure the minimum concentration of antibiotic that prevented planktonic growth from biofilms in antibiotic-free nutrient media (MBEC). MBEC indicates whether the exposure to antimicrobial agent used during the bMIC experiment sterilized biofilm-associated cells. MBEC values were generally larger than MICs and indicated an increased tolerance of stress exhibited by cells associated with biofilms. For C. crescentus, the MBEC values recapitulated the trend observed in the MSC: CCCP and DCAP effectively eradicated biofilm cells while ampicillin was not cytotoxic at the highest concentration tested (400 µM). CCCP was the only effective antibiotic against S. aureus biofilms. Since CCCP was not as effective as DCAP at killing stationary cells, it was hypothesized that this variability in efficacy of membrane-active drugs is in part caused by changes in membrane composition (i.e., membrane proteins and lipid content) at different developmental stages of bacterial cells. Despite the variations in efficacy, it was concluded that the comparison of MIC, bMIC, MSC, and MBEC measurements for the three antibiotics support the hypothesis that membrane-active drugs eradicate dormant, slow-growing bacteria more effectively than antibiotics that rely on growth-dependent mechanisms.

Example 8: Toxicity of DCAP in Mammalian Cells

To test the toxicity of DCAP against mammalian membranes, the hemolysis of rabbit red blood cells (RBC) was measured. These experiments were performed using conditions that closely mimicked the MIC and MSC assays. RBCs were treated with CCCP and DCAP at their MICs for the time periods used (17 hours) to determine the MIC of *C. crescentus* and *S. aureus*. After incubation, the absorbance of heme released from lysed RBCs was measured. The MIC concentrations of CCCP and DCAP did not significantly disrupt RBC membranes (FIG. 8A) although higher concentrations of DCAP (i.e., 50 μM) were moderately toxic to RBCs.

Figure 8:
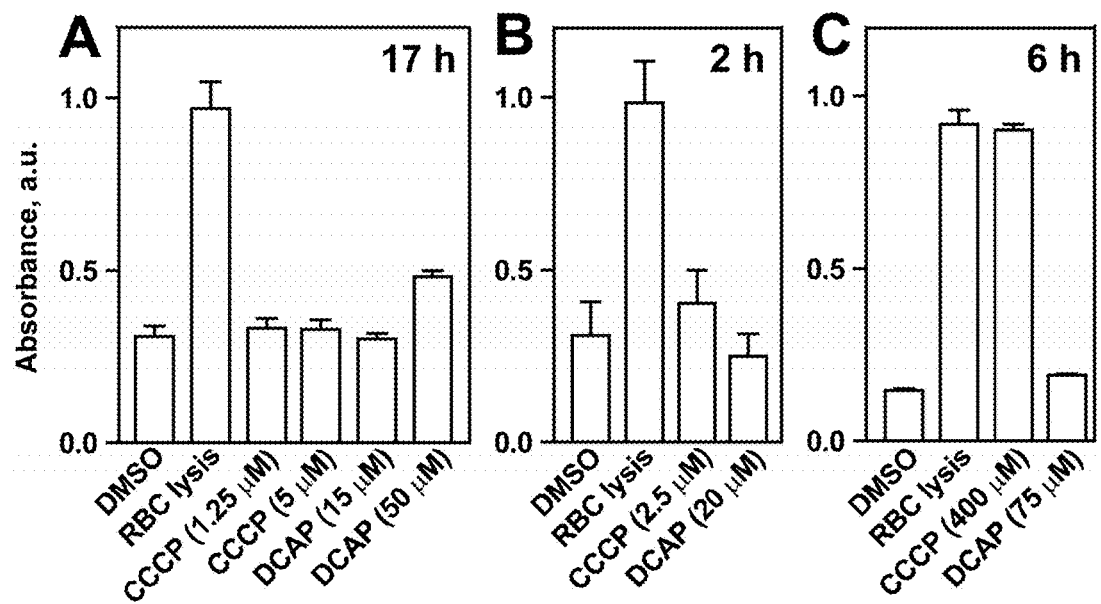
FIG. 8 shows a rabbit red blood cell (RBC) hemolysis assay. Columns represent average values, and error bars represent the standard deviation of the mean for three replicates. Assay performed using the MIC conditions for *C. crescentus* and *S. aureus* (A), the MSC for *C. crescentus* (B), and the MSC for *S. aureus* (C).

The MSC assay conditions were also reproduced to measure toxicity against RBCs. First, the minimum time required to obtain the MSC for DCAP treatment of *C. crescentus* (2 hours) and *S. aureus* (6 hours; data not shown) was determined. Using these times, the hemolysis assay was performed and no significant toxicity of DCAP against RBCs was observed (FIGS. 8B and C). In contrast, CCCP was toxic to RBCs at a high concentration (FIG. 8C). These measurements indicate that DCAP does not appreciably perturb mammalian membranes in conditions that are lethal to *C. crescentus* and *S. aureus*.

In summary, the discovery and characterization of the membrane-active antimicrobial agent DCAP and its analogs has been reported. DCAP kills bacteria by depolarizing $\Delta\Psi$ and increasing membrane permeability. These activities disrupt the organization and integrity of the bacterial membrane and mislocalize essential, membrane-associated proteins (e.g. MinD and FtsA). DCAP is inert to mammalian membranes at concentrations at which it is a potent antibacterial agent. Analogs of DCAP may yield more potent antimicrobial agents. Future studies with these compounds may provide insight into changes in the properties of membranes during the life cycle of bacteria and their correlation to the vulnerability of cells to membrane-active drugs.

Finally, studies of the structure-function relationship of DCAP and other broad-spectrum compounds may provide design rules for potent membrane-targeting drugs that kill bacterial cells specifically.

Example 9: Experimental Protocol for the General Synthesis of DCAP

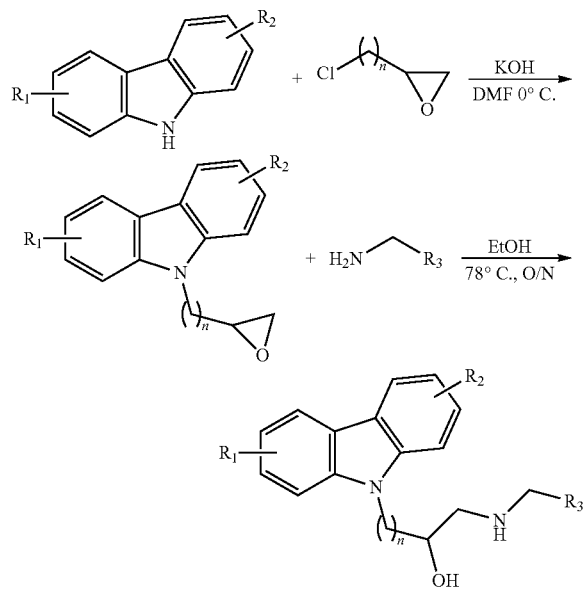

Scheme 1: General Synthetic Route for the Synthesis of DCAP Analogs

Synthetic Step 1: N-alkylation

In a dry round bottom flask, 3,6-dichlorocarbazole (705 mg, 3.0 mmol) was added to a solution of KOH (1.2 equiv., 3.6 mmol) in DMF (20 mL) at 0° C. After stirring the mixture for 30 min at 4° C., (+/−)-epichlorohydrin (2.5 equiv., 7.2 mmol) was added to the cooled flask drop wise. The reaction was stirred at 0° C. overnight. The reaction was removed from the ice bath and allowed to warm to room temperature. H₂O (20 mL) was added to the mixture and white solid precipitant formed. The heterogeneous mixture was filtered and washed with H₂O three times to provide a solid consisting of a mixture of N-alkylated product and remaining starting material. After applying high vacuum overnight, the white solid was used directly in any epoxide opening reaction.

Synthetic Step 2: Epoxide Opening

In a dry round bottom flask, the white solid from step 1 (100 mg, 0.344 mmol) was dissolved into ethanol (4 mL) and an amine (2 equiv., 0.68 mmol) was added to the mixture. The reaction was refluxed overnight under argon using an oil bath at 78° C. After cooling to room temperature, the ethanol was evaporated. The mixture was purified by flash column chromatography on silica gel with 5-20% methanol/dichloromethane to provide a DCAP analog.

Example 10: MIC Data for DCAP Analogs

Several analogs of DCAP have been synthesized and their activity against *E. coli* and other bacteria have been tested.

Bacterial Strains and Growth Conditions:

Luria-Bertani (LB) media (10 g/L tryptone, 10 g/L NaCl, 5 g/L yeast extract, pH 7.0) was used to grow all the strains represented in Tables 5 and 6. All the cultures were grown at 37° C. All the *E. coli* strains were grown while shaking at 200 rpm and the clinical pathogens were statically incubated.

Determination of the Minimum Inhibitory Concentration (MIC) of Bacterial Growth:

The MIC of *E. coli* strains was determined in liquid LB media in culture tubes (1 mL/tube) using the macrodilution method according to the CLSI guidelines as is known in the art. For clinical pathogenic organisms including *S. typhimurium, V. cholera, S. boydii, K pneumonia, E. aerogenes, A. baumannii, E. tarda,* and *M. morganii* strains, liquid LB media in 96-well microplates (100 μL/well) and the microdilution method from the CLSI guidelines were used.

TABLE 4

Chemical structures of the original DCAP (1) molecules and several analogs which have been synthesized since its discovery.

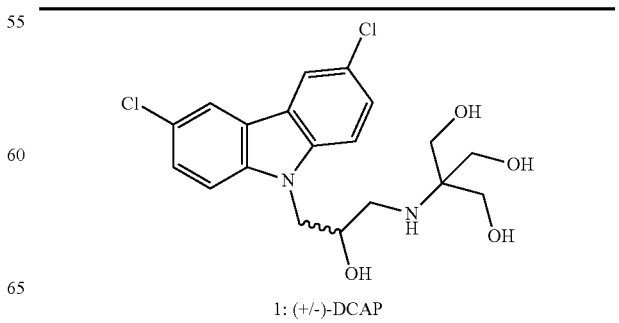

1: (+/−)-DCAP

TABLE 4-continued
Chemical structures of the original DCAP (1) molecules and several analogs which have been synthesized since its discovery.
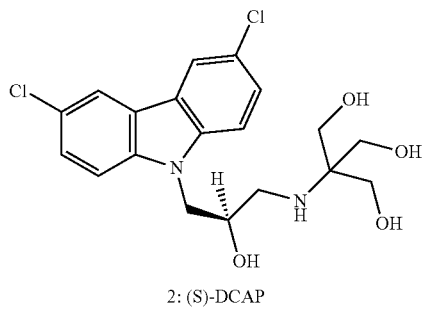 [SMILES: OCC(CO)(CO)NC[C@@H](O)Cn1c2ccc(Cl)cc2c2cc(Cl)ccc21]
2: (S)-DCAP
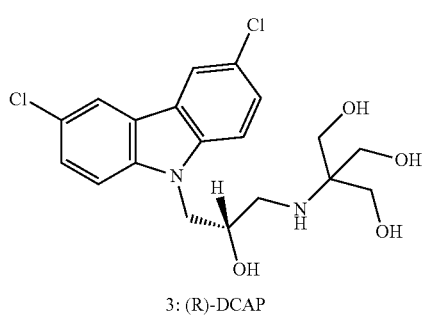 [SMILES: OCC(CO)(CO)NC[C@H](O)Cn1c2ccc(Cl)cc2c2cc(Cl)ccc21]
3: (R)-DCAP
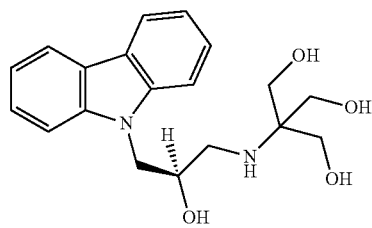
4: (+/−)-carbazole DCAP
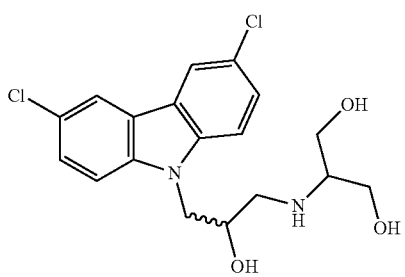
5: (+/−)-propanediol DCAP
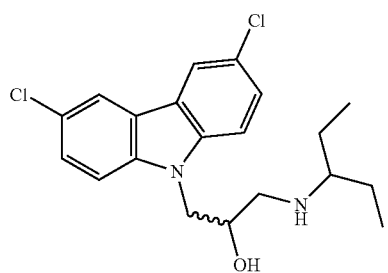
6: (+/−)-pentane DCAP
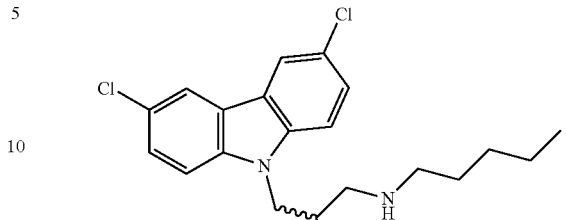
7: (+/−)-1-pentane DCAP
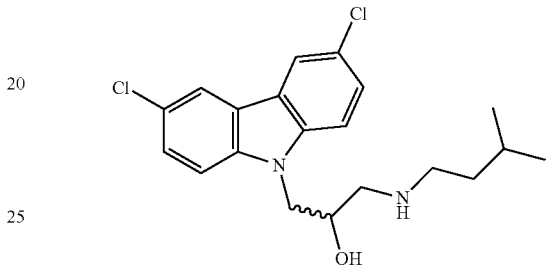
8: (+/−)-isopentyl DCAP
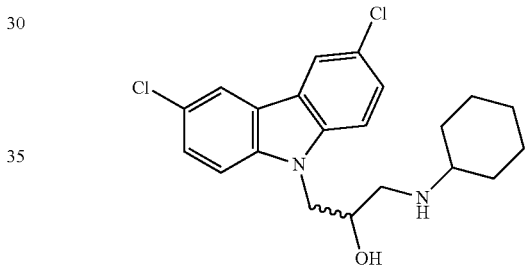
9: (+/−)-cyclohexyl DCAP
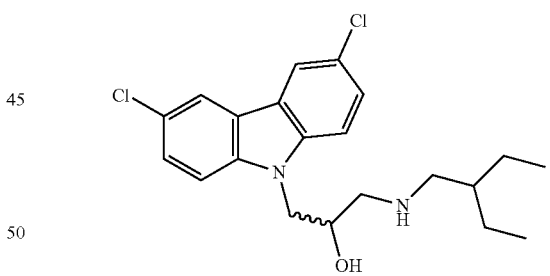
10: (+/−)-2-ethylbutane DCAP
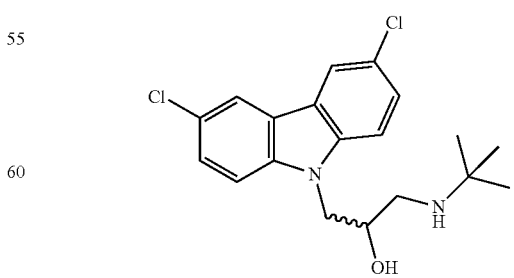
11: (+/−)-tert-butyl DCAP

TABLE 4-continued

Chemical structures of the original DCAP (1) molecules and several analogs which have been synthesized since its discovery.

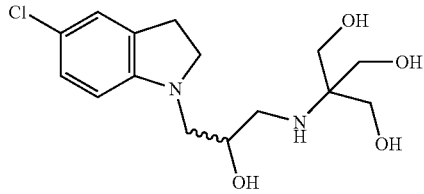

12: (+/-)-indole DCAP

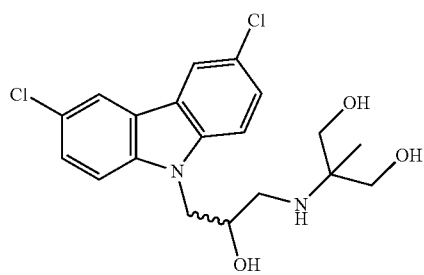

13: (+/-)-methyl-propandiol DCAP

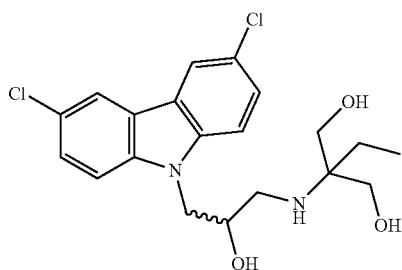

14: (+/-)-ethyl-propandiol DCAP

TABLE 5

MICs (μM) measured after incubation of ΔtolC E. coli strain with varying concentrations of each compound represented in Table 4.

| Compound | MIC (ΔtolC E. coli) |
|---|---|
| 1 | 20 |
| 2 | 20 |
| 3 | 20 |
| 4 | >80 |
| 5 | 20 |
| 6 | 5 |
| 7 | 5 |
| 8 | 2.5 |
| 9 | 2.5 |
| 10 | 2.5 |
| 11 | 40 |
| 12 | >40 |
| 13 | 40 |
| 14 | 20 |

TABLE 6

MICs (μM) measured after incubation of selected pathogenic strains with varying concentrations of each compound represented in Table 4.

| | MIC (uM) | | | |
|---|---|---|---|---|
| Organism/Strain | DCAP | 8 | 9 | 10 |
| E. coli BW25113 ΔtolC | 20 | 2.5 | 2.5 | 2.5 |
| Vibrio cholera | 50 | 6.25 | 25 | 6.25 |
| Salmonella typhimurium | 100 | 50 | >200 | 200 |
| Shigella boydii | 100 | 25 | 200 | 25 |
| Edwardsiella tarda | 100 | 25 | 200 | 12.5 |
| Klebsiella pneumonia | 200 | 50 | >200 | >200 |
| Enterobacter aerogenes | 200 | 50 | >200 | >200 |
| Acinetobacter baumannii | 200 | 12.5 | 100 | 25 |
| Morganella morganii | 200 | 50 | >200 | >200 |

The structure-activity relation studies provide insight into the regions of DCAP that modulate its biological activity. Modifications to the carbazole, heterocyclic ring reduced the MIC of the analogs, while changes to the tris-hydroxymethyl groups increased activity. Specifically, replacing the tris-hydroxymethyl groups with substituents that increased the hydrophobicity of the analog and decreased the MIC. These general rules provide a guide to the activity of additional analogs.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:
1. A method of treating a subject in need of treatment for a bacterial infection comprising administering to the subject a pharmaceutical composition comprising an antimicrobial compound of Formula I, or a pharmaceutically acceptable salt thereof, and a pharmaceutically acceptable excipient, wherein the antimicrobial compound of Formula I is:

G-Q-NH—C(R$^2$)(R$^3$)(R$^4$)  (I)

wherein
G is

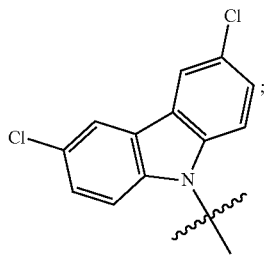 [SMILES: *n1c2ccc(Cl)cc2c2cc(Cl)ccc21]

Q is

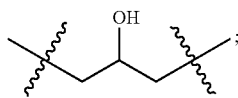 [SMILES: *CC(O)C*]

R$^2$ and R$^3$ are hydrogen, and
R$^4$ is C$_6$-C$_8$ alkyl optionally substituted with hydroxy, or
R$^2$ is hydrogen, and R$^3$ and R$^4$ in —C(R$^2$)(R$^3$)(R$^4$) together with the carbon (—C) form a C$_6$-C$_7$ cycloalkyl ring structure.

2. The method of claim 1, wherein the bacteria causing the infection are Gram-negative, bacteria, Gram-positive bacteria, or bacteria that are neither Gram-positive nor Gram-negative.

3. The method of claim 2, wherein the Gram-negative bacteria is *Escherichia coli, Caulobacter crescentus, Pseudomonas aeruginosa, Agrobacterium tumefaciens, Branhamella catarrhalis, Citrobacter diversus, Enterobacter aerogenes, Klebsiella pneumoniae, Proteus mirabilis, Pseudomonas aeruginosa, Salmonella typhimurium, Neisseria meningitidis, Serratia marcescens, Shigella sonnei, Shegella Boydii, Neisseria gonorrhoeae, Acinetobacter baumannii, Salmonella enteriditis, Fusobacterium nucleatum, Veillonella parvula, Bacteroides forsythus, Actinobacillus actinomycetemcomitans, Aggregatibacter actinomycetemcomitans, Porphyromonas gingivalis, Helicobacter pylori, Francisella tularensis, Yersinia pestis, Vibrio cholera, Morganella morganii, Edwardsiella tarda, Acinetobacter baumannii* or *Haemophilus influenzae*.

4. The method of claim 2, wherein the Gram-positive bacteria is a species of *Bacillus, Listeria, Staphylococcus, Streptococcus, Enterococcus, Corynebacterium, Propionibacterium* or *Clostridium*.

5. The method of claim 2, wherein the Gram-positive bacteria is *Staphylococcus aureus, Staphylococcus epidermidis, Enterococcus faecium,* or *Bacillus cereus*.

6. The method of claim 1, wherein the subject is a mammal.

7. The method of claim 6, wherein the mammal is a human.

8. A method of inhibiting bacterial growth comprising contacting bacteria with an antimicrobially effective amount of an antimicrobial compound of Formula I,
wherein the antimicrobial compound of Formula I is:

G-Q-NH—C(R$^2$)(R$^3$)(R$^4$)  (I)

wherein
G is

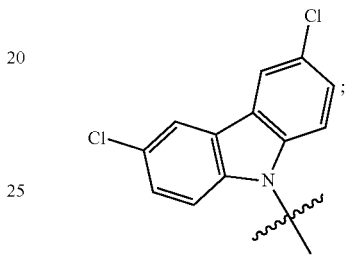

Q is

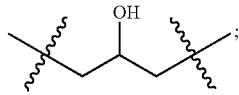

R$^2$ and R$^3$ are hydrogen, and
R$^4$ is C$_6$-C$_8$ alkyl optionally substituted with hydroxy, or
R$^2$ is hydrogen, and R$^3$ and R$^4$ in —C(R$^2$)(R$^3$)(R$^4$) together with the carbon (—C) form a C$_6$-C$_7$ cycloalkyl ring structure.

9. The method of claim 8, wherein the antimicrobial compound is 1-(cyclohexylamino)-3-(3,6-dichloro-9H-carbazol-9-yl)propan-2-ol; or 1-(3,6-dichloro-9H-carbazol-9-yl)-3-(2-ethylbutylamino)propan-2-ol.

10. The method of claim 8, wherein the bacteria are actively growing or are in the stationary phase.

11. The method of claim 8, wherein the bacteria are in the form of a biofilm.

12. The method of claim 1, wherein R$^3$ and R$^4$ are each independently C$_1$-C$_6$ alkyl optionally substituted with hydroxy, or R$^3$ and R$^4$ in —C(R$^2$)(R$^3$)(R$^4$) together with the carbon (—C) form a C$_3$-C$_7$ cycloalkyl ring structure.

13. The method of claim 1, wherein R$^2$ and R$^3$ are hydrogen, and R$^4$ is 2-ethylbutane; or wherein R$^2$ is hydrogen and R$^3$ and R$^4$ in —C(R$^2$)(R$^3$)(R$^4$) together with the carbon (—C) form a cyclohexyl.

* * * * *